(12) United States Patent
Hill

(10) Patent No.: US 7,812,965 B2
(45) Date of Patent: Oct. 12, 2010

(54) MULTIPLE-DEGREE OF FREEDOM INTERFEROMETER WITH COMPENSATION FOR GAS EFFECTS

(75) Inventor: Henry A. Hill, Tucson, AZ (US)

(73) Assignee: Zygo Corporation, Middlefield, CT (US)

( * ) Notice: Subject to any disclaimer, the term of this patent is extended or adjusted under 35 U.S.C. 154(b) by 235 days.

(21) Appl. No.: 12/001,662

(22) Filed: Dec. 11, 2007

(65) Prior Publication Data

US 2008/0285051 A1    Nov. 20, 2008

Related U.S. Application Data

(60) Provisional application No. 60/869,482, filed on Dec. 11, 2006, provisional application No. 60/898,083, filed on Jan. 29, 2007.

(51) Int. Cl.
*G01B 11/02* (2006.01)
(52) U.S. Cl. ..................................... 356/500
(58) Field of Classification Search ............... 356/486, 356/487, 493, 500
See application file for complete search history.

(56) References Cited

U.S. PATENT DOCUMENTS

| | | | |
|---|---|---|---|
| 4,685,803 A | 8/1987 | Sommargren | |
| 4,688,940 A | 8/1987 | Sommargren et al. | |
| 4,733,967 A | 3/1988 | Sommargren | |
| 4,948,254 A | 8/1990 | Ishida | |
| 5,404,222 A | 4/1995 | Lis | |
| 5,537,209 A | 7/1996 | Lis | |
| 5,552,888 A | 9/1996 | Sogard et al. | |
| 5,764,362 A | 6/1998 | Hill et al. | |
| 5,838,485 A | 11/1998 | de Groot et al. | |
| 6,137,574 A | 10/2000 | Hill | |
| 6,198,574 B1 | 3/2001 | Hill | |
| 6,201,609 B1 | 3/2001 | Hill | |
| 6,246,481 B1 | 6/2001 | Hill | |
| 6,252,668 B1 | 6/2001 | Hill | |
| 6,330,065 B1 | 12/2001 | Hill | |
| 6,407,816 B1 | 6/2002 | de Groot et al. | |
| 6,430,465 B2 | 8/2002 | Cutler | |

(Continued)

FOREIGN PATENT DOCUMENTS

EP        0 843 152        5/1998

(Continued)

OTHER PUBLICATIONS

International Search Report.

(Continued)

*Primary Examiner*—Tarifur Chowdhury
*Assistant Examiner*—Jonathon D Cook
(74) *Attorney, Agent, or Firm*—Fish & Richardson P.C.

(57) ABSTRACT

The disclosure features multiple degree-of-freedom interferometers (e.g., non-dispersive interferometers) for monitoring linear and angular (e.g., pitch and/or yaw) displacements of a measurement object with compensation for variations in the optical properties of a gas in the interferometer measurement (and/or reference) beam paths. The disclosure also features interferometry systems that feature an array of interferometers (e.g., including one or more multiple degree-of-freedom interferometer), each configured to provide different information about variations in the optical properties of the gas in the system. Multiple degree-of-freedom interferometers are also referred to as multi-axis interferometers.

40 Claims, 12 Drawing Sheets

U.S. PATENT DOCUMENTS

| | | |
|---|---|---|
| 6,495,847 B1 | 12/2002 | Asano et al. |
| 6,529,279 B2 | 3/2003 | de Groot et al. |
| 6,573,996 B1 | 6/2003 | Deliwala et al. |
| 6,757,066 B2 | 6/2004 | Hill |
| 6,765,195 B1 | 7/2004 | Leviton |
| 6,775,009 B2 | 8/2004 | Hill |
| 6,778,280 B2 | 8/2004 | de Groot et al. |
| 6,806,961 B2 | 10/2004 | Hill |
| 6,819,434 B2 | 11/2004 | Hill |
| 6,839,141 B2 | 1/2005 | Hill |
| 6,842,256 B2 | 1/2005 | Hill |
| 6,888,638 B1 | 5/2005 | Hill |
| 6,891,624 B2 | 5/2005 | Hill |
| 6,937,349 B2 | 8/2005 | Jones et al. |
| 6,950,192 B2 | 9/2005 | Hill |
| 7,012,700 B2 | 3/2006 | de Groot et al. |
| 7,038,850 B2 | 5/2006 | Chang et al. |
| 7,075,619 B2 | 7/2006 | Hill |
| 7,106,454 B2 | 9/2006 | de Groot et al. |
| 7,139,081 B2 | 11/2006 | de Groot |
| 7,268,888 B2 | 9/2007 | Hill |
| 7,280,223 B2 | 10/2007 | Hill |
| 7,280,224 B2 | 10/2007 | Hill |
| 7,283,248 B2 | 10/2007 | Hill |
| 7,362,446 B2 | 4/2008 | Van Der Pasch et al. |
| 7,528,961 B2 | 5/2009 | Hill |
| 2003/0048458 A1 | 3/2003 | Mieher et al. |
| 2003/0164948 A1* | 9/2003 | Hill ............................. 356/487 |
| 2003/0179357 A1 | 9/2003 | Ravensbergen |
| 2004/0263846 A1 | 12/2004 | Kwan |
| 2005/0018162 A1 | 1/2005 | Leenders et al. |
| 2005/0151951 A1 | 7/2005 | Hill |
| 2006/0256346 A1 | 11/2006 | Hill |
| 2008/0285051 A1 | 11/2008 | Hill |

FOREIGN PATENT DOCUMENTS

| | | |
|---|---|---|
| JP | 60-225005 | 11/1985 |
| JP | 64-18002 | 1/1989 |
| JP | 11-108614 | 4/1999 |
| JP | 11-230716 | 8/1999 |
| WO | WO 00/65302 | 11/2000 |

OTHER PUBLICATIONS

International Preliminary Report on Patentability issued on Jun. 24, 2009, corresponding to Int'l. Appln. No. PCT/US2007/088708, filed Dec. 21, 2007.
U.S. Appl. No. 60/859,348, filed Nov. 2006, Hill.
U.S. Appl. No. 60/859,693, filed Nov. 2006, Hill.
U.S. Appl. No. 60/862,949, filed Oct. 2006, Hill.
U.S. Appl. No. 60/869,483, filed Dec. 2006, Hill.
U.S. Appl. No. 60/869,482, filed Dec. 2006, Hill.
U.S. Appl. No. 10/218,968, filed Aug. 2002, Byoung-Sun Na.
Lis, Steven A.,"An Air Turbulence Compensated Interferometer for IC Manufacturing," SPIE 2440, [p. 467 (1995).
Arfken, G. "Gibbs Phenomenon", Mathematical Methods For Physicists, Academic Press (1966).
Bobroff, N., "Residual Errors In Laser Interferometry From Air Turbulence And Nonlinearity", Appl. Opt 26(13), pp. 907-926 (1987).
Bobroff, N., "Recent Advances In Displacement Measuring Interferometry," Measurement Science & Tech. 4(9), pp. 907-926 (1993).
Estler, W.T., "High-Accuracy Displacement Interferometry In Air," Appl. Opt. 24(6), pp. 808-815 (1985).
Jones, F.E., "The Refractivity Of Air", J. Res. NBS 86(1), pp. 27-32 (1981).
Ishida, Akira, "Two Wavelength Displacement-Measuring Interferometer Using Second-Harmonic Light To Eliminate Air-Turbulence-Induced Errors," Jpn. J. Appl. Phys. 28(3), L473-475 (1989).
Zanoni, C., "Differential Interferometer arrangements for distance and angle measurements: Principles, advantages and applications", VDI Berichte Nr. 749, pp. 93-106 (1989).
Zhu, Y. et al., "Long-Arm Two-Color Interferometer For Measuring The Change Of Air Refractive Index," SPIE 1319, Optics in Complex Systems, pp. 538-539 (1990).
International Search Report and Written Opinion for Int'l. Appln. No. PCT/US2006/043494 dated Mar. 20, 2008.

* cited by examiner

MULTIPLE-DEGREE OF FREEDOM INTERFEROMETER WITH COMPENSATION FOR GAS EFFECTS

CROSS REFERENCE TO RELATED APPLICATIONS

Under 35 U.S.C. 119(e)(1), this application claims benefit of Provisional Patent Application No. 60/869,482, entitled "MULTIPLE-DEGREE OF FREEDOM HIGH STABILITY PLANE MIRROR INTERFEROMETER WITH COMPENSATION FOR TURBULENCE EFFECTS," filed on Dec. 11, 2006, and to Provisional Patent Application No. 60/898,083, entitled "MEASUREMENT AND COMPENSATION OF STATIONARY NON-RANDOM EFFECTS OF GAS AND OTHER GAS RELATED EFFECTS ON OPTICAL PATH LENGTHS OF MULTI-AXIS INTERFEROMETERS," filed on Jan. 29, 2007. The entire contents of both Provisional Patent Application No. 60/869,482 and Provisional Patent Application No. 60/898,083 are incorporated herein by reference.

BACKGROUND

Lithography systems are commonly used in fabricating large-scale integrated circuits such as computer chips and the like. The function of a lithography system is to direct spatially patterned radiation onto a photoresist-coated wafer. The process involves determining which location of the wafer is to receive the radiation (alignment) and applying the radiation to the photoresist at that location (exposure).

In general, a lithography system, also referred to as a lithography tool, an exposure system or an exposure tool, typically includes an illumination system and a wafer positioning system. The illumination system includes a radiation source for providing radiation such as ultraviolet, visible, x-ray, electron, or ion radiation, and a reticle or mask for imparting the pattern to the radiation, thereby generating the spatially patterned radiation. In addition, for the case of reduction lithography, the illumination system can include a lens assembly for imaging the spatially patterned radiation onto the wafer. The imaged radiation exposes resist coated onto the wafer. The illumination system also includes a mask stage for supporting the mask and a positioning system for adjusting the position of the mask stage relative to the radiation directed through the mask. The wafer positioning system includes a wafer stage for supporting the wafer and wafer chuck and a positioning system for adjusting the position of the wafer stage relative to the imaged radiation. Fabrication of integrated circuits can include multiple exposing steps. For a general reference on lithography, see, for example, J. R. Sheats and B. W. Smith, in *Microlithography: Science and Technology* (Marcel Dekker, Inc., New York, 1998), the contents of which is incorporated herein by reference.

During exposure, the radiation source illuminates the patterned reticle, which scatters the radiation to produce the spatially patterned radiation. The reticle is also referred to as a mask, and these terms are used interchangeably below. In the case of reduction lithography, a reduction lens collects the scattered radiation and forms a reduced image of the reticle pattern. Alternatively, in the case of proximity printing, the scattered radiation propagates a small distance (typically on the order of microns) before contacting the wafer to produce a 1:1 image of the reticle pattern. The radiation initiates photo-chemical processes in the resist that convert the radiation pattern into a latent image within the resist.

Interferometry metrology systems herein after referred to simply as interferometer systems are typically important components of the positioning mechanisms that control the positions of the wafer and reticle and register the reticle image on the wafer. Interferometry systems can be used to precisely measure the positions of each of the wafer stage and mask stage relative to other components of the exposure system, such as the lens assembly, radiation source or support structure. In such cases, the interferometry system can be attached to a stationary structure and a measurement object attached to a movable element such as one of the mask and wafer stages. Alternatively, the situation can be reversed, with the interferometry system attached to a movable object and the measurement object attached to a stationary object.

More generally, such interferometry systems can be used to measure the position of any one component of the exposure system relative to any other component of the exposure system, in which the interferometry system is attached to, or supported by, one of the components and the measurement object is attached, or is supported by the other of the components.

There are various reasons that favor the operation of a lithography tool with the cavity of the lithography tool filled with a gas instead of where the cavity is evacuated. However, the presence of a dispersive medium such as the gas in the measurement and reference paths of an interferometric system used to monitor the position of the stage or stages of the lithography tool introduces uncertainty in measurements made using the interferometric system due to the atmospheric effects.

A difficult measurement related to the refractive index of a gas is the compensation of refractive index fluctuations over a measurement path of unknown or variable length, with uncontrolled temperature and pressure. An example situation is high-precision distance measuring interferometry, such as is employed in micro-lithographic fabrication of integrated circuits. See for example an article entitled "Residual Errors In Laser Interferometry From Air Turbulence And Nonlinearity," by N. Bobroff, *Appl. Opt.* 26(13), pp 2676-2682 (1987), and an article entitled "Recent Advances In Displacement Measuring Interferometry," also by N. Bobroff, *Measurement Science & Tech.* 4(9), pp 907-926 (1993). As noted in the aforementioned cited references, interferometric displacement measurements in a gas are subject to environmental uncertainties, particularly to changes in air pressure and temperature; to uncertainties in air composition such as resulting from changes in humidity; and to the effects of turbulence in the gas. Such factors alter the wavelength of the light used to measure the displacement. Under normal conditions the refractive index of air for example is approximately 1.0003 with a variation of the order of $1\times10^{-5}$ to $1\times10^{-4}$. In many applications the refractive index of air must be known with a relative precision of less than 0.1 ppm (parts per million) to less than 0.001 ppm, these two relative precisions corresponding to a displacement measurement accuracy of 100 nm and less than 1 nm, respectively, for a one meter interferometric displacement measurement.

There are frequent references in the art to heterodyne methods of phase estimation, in which the phase varies with time in a controlled way. For example, in a known form of prior-art heterodyne distance-measuring interferometer, the source emits two orthogonally polarized beams having slightly different optical frequencies (e.g. 2 MHz). The interferometric receiver in this case is typically comprised of a linear polarizer and a photodetector to measure a time-varying interference signal. The signal oscillates at the beat frequency and the phase of the signal corresponds to the relative phase difference. A further representative example of the prior art in heterodyne distance-measuring interferometry is taught in commonly owned U.S. Pat. No. 4,688,940 issued to G. E. Sommargren and M. Schaham (1987). These known forms of interferometric metrology do not generally compensate for fluctuations in refractive index of a gas in a measurement path of an interferometer.

One way to detect refractive index fluctuations is to measure changes in pressure and temperature along a measurement path and calculate the effect on the optical path length of the measurement path. Mathematical equations for effecting this calculation are disclosed in an article entitled "The Refractivity Of Air," by F. E. Jones, *J. Res. NBS* 86(1), pp 27-32 (1981). An implementation of the technique is described in an article entitled "High-Accuracy Displacement Interferometry In Air," by W. T. Estler, *Appl. Opt.* 24(6), pp 808-815 (1985). This technique provides approximate values, is cumbersome, and corrects for slow, global fluctuations in air density.

Another, more direct way to detect the effects of a fluctuating refractive index over a measurement path is by multiple-wavelength distance measurement. The basic principle may be understood as follows. Interferometers and laser radar measure the optical path length between a reference and an object, most often in open air. The optical path length is the integrated product of the refractive index and the physical path traversed by a measurement beam. In that the refractive index varies with wavelength, but the physical path is independent of wavelength, it is generally possible to determine the physical path length from the optical path length, particularly the contributions of fluctuations in refractive index, provided that the instrument employs at least two wavelengths. The variation of refractive index with wavelength is known in the art as dispersion and this technique is often referred to as the dispersion technique.

An example of a two-wavelength distance measurement system is described in an article by Y. Zhu, H. Matsumoto, T. O'ishi, *SPIE* 1319, Optics in Complex Systems, pp 538-539 (1990), entitled "Long-Arm Two-Color Interferometer For Measuring The Change Of Air Refractive Index." The system of Zhu et al. employs a 1064 nm wavelength YAG laser and a 632 nm HeNe laser together with quadrature phase detection. Substantially the same instrument is described in Japanese in an earlier article by Zhu et al. entitled "Measurement Of Atmospheric Phase And Intensity Turbulence For Long-Path Distance Interferometer," Proc. 3rd Meeting On Lightwave Sensing Technology, *Appl. Phys. Soc. of Japan,* 39 (1989). The interferometer of Zhu et al. has insufficient resolution for applications that require sub-micron interferometry such as microlithography.

An example of a two-wavelength high-precision interferometry system for microlithography is represented by U.S. Pat. No. 4,948,254 issued to A. Ishida (1990). A similar device is described by Ishida in an article entitled "Two Wavelength Displacement-Measuring Interferometer Using Second-Harmonic Light To Eliminate Air-Turbulence-Induced Errors," *Jpn. J. Appl. Phys.* 28(3), L473-475 (1989). In the article, a displacement-measuring interferometer is disclosed which eliminates errors caused by fluctuations in the refractive index by means of two-wavelength dispersion detection. An Ar+ laser source provides both wavelengths simultaneously by means of a frequency-doubling crystal known in the art as BBO. The use of a BBO doubling crystal results in two wavelengths that are fundamentally phase locked, thus greatly improving the stability and accuracy of the refractive index measurement. However, the motion of the object results in rapid variations in phase that make it difficult to detect accurately the effects of fluctuations in the refractive index.

In U.S. Pat. No. 5,404,222 entitled "Interferometric Measuring System With Air Turbulence Compensation," issued to S. A. Lis (1995), there is disclosed a two-wavelength interferometer employing the dispersion technique for detecting and compensating refractive index fluctuations. A similar device is described by Lis in an article entitled "An Air Turbulence Compensated Interferometer For IC Manufacturing," *SPIE* 2440 (1995). Improvement on U.S. Pat. No. 5,404,222 by S. A. Lis is disclosed in U.S. Pat. No. 5,537,209. The principal innovation of this system with respect to that taught by Ishida in *Jpn. J. Appl. Phys.* (supra) is the addition of a second BBO doubling crystal to improve the precision of the phase detection means. The additional BBO crystal makes it possible to optically interfere two beams having wavelengths that are exactly a factor of two different. The resultant interference has a phase that is directly dependent on the refractive index but is substantially independent of stage motion.

Two two-wavelength distance measuring systems based on superheterodyne techniques are described in commonly owned U.S. Pat. No. 5,764,362 entitled "Superheterodyne Method And Apparatus For Measuring The Refractive Index Of Air Using Multiple-Pass Interferometry" by Henry A. Hill and P. de Groot and U.S. Pat. No. 5,838,485 entitled "Superheterodyne Interferometer And Methods For Compensating The Refractive Index Of Air Using Electronic Frequency Multiplication" by Peter de Groot and Henry A. Hill. The contents of both of the two cited patents are herein incorporated in their entirety by reference. In both of the two referenced patents, contributions to measured phases due to effects of a gas in a measurement path are directly dependent on the refractive index but the contributions due to stage motion are substantially reduced. The first of the two referenced patents is based on multiple pass interferometry and the second referenced patent is based on electronic frequency multiplication.

Other commonly owned U.S. patents relating to dispersion interferometry are U.S. Pat. No. 6,330,065 B1, U.S. Pat. No. 6,327,039 B1, U.S. Pat. No. 6,407,866, U.S. Pat. No. 6,525,825, U.S. Pat. No. 6,525,826 B2, U.S. Pat. No. 6,529,279 and U.S. Pat. No. 6,219,144 B1. The contents of the other commonly owned cited patents are herein incorporated in their entirety by reference.

A commonly owned U.S. Patent relating to the measurement of intrinsic properties of a gas such as the reciprocal dispersive power is U.S. Pat. No. 6,124,931 (Γ monitor). The contents of the commonly owned cited patent are herein incorporated in their entirety by reference.

A non-dispersive apparatus and method for the compensation of turbulent effects of a gas is described in commonly owned U.S. patent application Ser. No. 10/350,522 entitled "Method and Apparatus For Compensation Of Time-varying Optical Properties of Gas In Interferometry" by Henry A. Hill. Patent application Ser. No. 10/350,522 compensates for turbulent effects of the gas on the direction of propagation of a first beam by using measured effects of the gas turbulence on the directions of propagation of the first beam and a second beam. The first and second beams are spatially separated and the directions of propagation of the first and second beams are substantially parallel. Gas turbulence effects on the measurement path length of the first beam are compensated by using the measured turbulent effects of changes in the direction of propagation of the first beam over the measurement path length and a known relationship between the effects of gas turbulence on the direction of propagation of a beam and on the corresponding effects on the optical path length. The contents of cited patent application Ser. No. 10/350,522 are incorporated herein in their entirety by reference.

Another non-dispersive apparatus and method for the compensation of turbulent effects of a gas is described in commonly owned U.S. patent application Ser. No. 10/701,759 entitled "Compensation of Refractivity Perturbations In A Measurement Path Of An Interferometer" by Henry A. Hill. Patent application Ser. No. 10/701,759 compensates for turbulent effects of the gas on the optical path length of a beam or the average optical path length of two beams of an interferometer system by using measured differential effects of the gas turbulence at a single wavelength on the relative measurement path lengths of a first beam and a second beam wherein cells of the gas that pass through the measurement path of the first beam are subsequently transported through the measurement path of the second beam. The directions of propagation of the spatially separated first and second beams are substantially parallel. The contents of cited U.S. patent application Ser. No. 10/701,759 are incorporated herein in their entirety by reference.

Another non-dispersive apparatus and method for the compensation for turbulence effects of a gas is described in commonly owned U.S. Provisional Application No. 60/676,190 entitled "Compensation of Turbulent Effects Of Gas In Measurement Paths of Multi-Axis Interferometers," the corresponding utility application Ser. No. 11/413,917, and the CIP of U.S. patent application Ser. No. 11/413,917 also entitled "Compensation of Turbulent Effects Of Gas In Measurement Paths of Multi-Axis Interferometers." The provisional and the two utility applications are by Henry A. Hill and the contents of the cited provisional and the two utility applications are incorporated herein in their entirety by reference.

The effects of stationary changes in the optical path length of measurement paths at a single wavelength are compensated by using a procedure such as described in commonly owned U.S. Pat. No. 7,075,619 B2 entitled "In-Process Correction of Stage Mirror Deformations During a Photolithography Exposure Cycle" and U.S. Pat. No. 6,842,256 entitled "Compensation For Effects Of Variations In Gas Refractivity In Interferometers." The two U.S. patents are by Henry A. Hill and the contents of both thereof are incorporated herein in their entirety by reference.

SUMMARY

The disclosure features multiple degree-of-freedom interferometers (e.g., non-dispersive interferometers) for monitoring linear and angular (e.g., pitch and/or yaw) displacements of a measurement object with compensation for variations in the optical properties of a gas in the interferometer measurement (and/or reference) beam paths. The disclosure also features interferometry systems that feature an array of interferometers (e.g., including one or more multiple degree-of-freedom interferometer), each configured to provide different information about variations in the optical properties of the gas in the system. Multiple degree-of-freedom interferometers are also referred to as multi-axis interferometers.

Variations in the optical properties of gas in interferometer beam in a lithography tool can result from a number of different sources. For example, turbulence in a gas is one source of such variations. In general, these sources can be classified as due to stationary or random effects. As used herein, "stationary" refers to effects where the probability-space parameters of a process classified as stationary are invariant under a translation in time modulo a time interval. In other words, the mean and variance of the relevant probability-space parameters are related at equivalent stages, e.g., of each exposure cycle of a lithography tool. The aforementioned time interval for a given lithography tool, for example, can be the reciprocal of the rate at which wafers are processed by the tool. Stationary non-random effects of a gas and other gas related effects can be further classified according to whether the effect is generated by an adiabatic or non-adiabatic process and according to whether the spatial distribution of the effect is nominally isotropic or non-isotropic. Stationary non-random effects are generally different from turbulence effects in both temporal and spatial properties. With respect to temporal properties, turbulence effects are characterized as a non-stationary effect in comparison to the temporal properties of stationary non-random effects. With respect to spatial properties, stationary effects generally exhibit stationary spatial patterns in addition to stationary temporal properties. The ordering of the stationary non-random effects of a gas and other gas related effects can be used in the design of the processing of information obtained from the multi-axis interferometers and/or other interferometers in an interferometric system.

An adiabatic change in the optical properties (e.g., refractivity) of the gas is the result of changes in gas pressure that occur on time scales set by the speed of sound and the size of an associated cavity. These include acoustic perturbations in a system. A non-adiabatic isotropic change in the optical properties of the gas is the result of changes in gas density and/or composition that, e.g., are nominally spatially isotropic in a plane. The non-adiabatic isotropic changes in gas density and/or composition are classified as nominally isotropic when the spatial wavelength of a Fourier component of a change is of the order of or greater than twice a spatial scale equal to a measurement beam path length of an interferometer used to detect the respective change and classified as non-adiabatic when the Fourier component of the change is transported as a Lagrangian perturbation, i.e., the Fourier component of the change is transported with the flow of the gas. Non-adiabatic non-isotropic changes in the gas density and/or composition are classified as nominally non-isotropic when the spatial wavelength of a Fourier component of a change is less than of the order of twice a spatial scale equal to a measurement beam path length of an interferometer used to detect the respective change and classified as non-adiabatic when the Fourier component of the change is transported as a Lagrangian perturbation.

In certain embodiments, adiabatic effects scale between different interferometers in the interferometry system according to lengths of the respective relative measurement path lengths with time delays generally less than ~3 msec for cavities with dimensions of the order of 1 m. Non-adiabatic effects can exhibit characteristic time delays between interferometers of the array of interferometers determined by a component of the velocity of gas flow and respective spatial separation. For an example of a corresponding component of the velocity of gas flow of 0.5 m/sec and an example of a respective spatial separation of 0.025 m, the characteristic time delay is approximately 50 msec. Isotropic effects scale between different interferometers of the array of interferometers according to lengths of the respective relative measurement path lengths of the interferometers.

In addition to the contributions of stationary non-random effects of a gas and other gas related effects, there can be other contributions to phases measured by interferometers in an interferometry system. For example, the other contributions to measured phases in lithography tools can include oscillations of components of a photolithographic apparatus, stationary effects such as for example body deformation of the photolithographic apparatus generated by motion of a stage, and non-stationary effects such as for example body deformation of the photolithographic apparatus from thermal drift. The effects of the other contributions are measured and compensated or eliminated in disclosed embodiments.

In some embodiments, an array of interferometers including multi-axis interferometers is used in conjunction with stored information, e.g., look up tables, power series or orthogonal representations, about stationary effects to obtain information about each of the contributions classified as adiabatic, non-adiabatic isotropic, and non-adiabatic non-isotropic. The interferometers can be configured to yield three or more independent measurements that have differing sensitivities to each of the contributions.

In some embodiments, interferometry systems include a multi-axis displacement measuring interferometer in conjunction with one or more interferometers having a fixed measurement path. Fixed path interferometers can be used, for example, to provide additional compensation for variations in the optical properties of the gas and/or compensation for other sources of uncertainty in measurements made using the interferometry system. In some embodiments, such as where the interferometry system is used in a lithography tool, a column reference interferometer (CRI) can be used to provide additional compensation.

Alternatively, or additionally, one or more isolated path reference interferometers (also referred to as longitudinal reference interferometers, or LRI's) can be used to provide additional compensation for variations in the optical properties of the gas. Isolated path reference interferometers have a measurement path that is both fixed in length and thermally isolated from the gas environment in which the interferometer is placed. Accordingly, variations in the phase monitored using an LRI are, in general, due to adiabatic changes in the system or changes in the wavelength of the input beam.

In some embodiments, non-dispersive apparatus are used to compensate, e.g., by a factor about 10 or more, for effects of turbulence on the optical properties of the gas that exhibit temporal frequencies of the order of the inverse of a spacing between different measurement beam paths of a multi-axis interferometer times the characteristic speed of gas flow across the paths of the multi-axis interferometer.

Embodiments include processing of a first difference parameter (FDP) wherein neither accurate knowledge of the orientation or position of a respective measurement and/or reference object mirrors of the interferometer is required. In certain embodiments, measurement of FDP is made with a plane mirror interferometer configured with multiple-measurement beam paths such that FDP is based on multiple single pass linear displacement measurements of the measurement object mirror. The FDP can be invariant to displacements of the measurement object mirror in the direction orthogonal to the respective mirror surface that may occur prior to and/or during the acquisition of the linear displacement measurements and are invariant up through first order effects with respect to changes in orientation of the mirrors. Other second and higher order difference parameters may also be beneficially used.

FDP can be related to first and higher order temporal and/or spatial derivatives of effects on measured optical paths of gas turbulence and acoustic perturbations of gas properties. The first and higher order temporal or spatial derivatives of the effects are inverted either by combinations of Fourier transforms and associated inverse Fourier transforms, by direct integrations with respect to the corresponding temporal or spatial coordinates, or by use of Fourier series techniques to generate a contemporaneous measurement of gas turbulence effects and acoustic perturbation effects on measurements of linear and angular displacements of objects by the interferometer. The contemporaneously measured values are used for compensating the gas turbulence effects and acoustic perturbation effects of gas properties on the measurements of linear and angular displacements of objects.

In some embodiments, measurements of gas turbulence and acoustic effects on the optical path lengths of reference and measurement beams are achieved by conditioning an input beam prior to directing the input beam to reference and measurement objects of the interferometer. Beam shear can also be reduced (e.g., eliminated) in an interferometric system by the conditioning of the input beam. Accordingly, in certain aspects, the disclosure features apparatus and methods for enabling measurements of gas turbulence and acoustic effects and reducing beam shear in an interferometer and/or for reducing beam shear of measurement beams at the reference and measurement objects of an interferometer. Conditioning the input beam can reduce beam shear associated with changes in the position (e.g., orientation and/or displacement relative to a reference frame) of a measurement object (e.g. plane mirror or retroreflector). Conditioning the input beam refers to adjusting the relative direction of propagation and/or location of the beam relative to a reference system to compensate for changes in the beam's path in the interferometer that are introduced by changes in the measurement object orientation. Conditioning of the input beam can be achieved passively.

Embodiments can include a section that conditions properties of an input beam to form a conditioned input beam, which is then directed to an interferometer. The interferometer splits the conditioned input beam into a measurement beam and a reference beam. The beam conditioning section can include components that compensate for changes in the propagation of the measurement beam that would be caused by changes in the orientation of the measurement object. The beam conditioning section can also include components that compensate for beam shear that may be introduced during the beam conditioning to minimize shear of the conditioned input beam at the interferometer and/or at the measurement object.

Other beams can be derived from the conditioned input beam prior to the interferometer. For example, a portion of the conditioned input beam can be directed to a first detector for determining a change in an orientation of the measurement object. Alternatively, or additionally, a portion of the conditioned input beam can be directed to an angle interferometer such as described in subsequently referenced U.S. Pat. No. 6,563,593 B2, U.S. Pat. No. 6,552,804 B2, and U.S. Pat. No. 6,917,432. Angle interferometers can be used to monitor changes in the direction of propagation of the conditioned input beam relative to an optical axis defined by the beam conditioning portion.

For embodiments where the measurement object is a plane mirror, conditioning the input beam can cause the measurement beam to have a direction of propagation that is substantially orthogonal to the reflecting surface of the plane mirror for a range of orientation angles. As the orientation of the measurement object varies within this range of angles, beam conditioning ensures that the measurement beam retains normal incidence at the measurement object. Accordingly, shear between the reference and measurement components both within the interferometer, in the output beam, and at the measurement object that could result from such changes in measurement object orientation is reduced. Effects of gas turbulence and acoustic perturbations can be reduced in the conditioned input beam (e.g., eliminated). Alternatively, or additionally, effects on properties of the conditioned input beam from departures of the surface of the measurement object from a reference plane mirror surface can be reduced (e.g., eliminated up through first order spatial derivatives).

In addition, the reference and measurement beam components of the conditioned input beam can have substantially zero shears at the input of one or more interferometers used to measure changes in the position of the measurement object.

In embodiments, the measurement object is used as an integral part of the apparatus in conditioning the input beam to form the conditioned input beam. The input beam is typically directed to contact the measurement object at least once in the conditioning portion of the apparatus. In heterodyne interferometry, both frequency components of the input beam are directed to contact measurement object. Accordingly, any change in the position of the measurement object from a reference position causes a change in the propagation direction/beam location relative to a path defined by the reference position.

In some embodiments, interferometers are used in conjunction with a planar encoder apparatus for measuring and compensating stationary non-random effects of a gas and other gas related effects on accuracy of interferometric measurements. Stationary non-random effects not related to the gas and vibrations that affect the measurement and compensation for the stationary non-random effects of the gas and the other gas related effects can also be measured and compensated.

The interferometric and planar encoder apparatus and method used in disclosed embodiments comprise apparatus and methods for the compensation of stationary non-random effects of a gas and other related effects of the gas on accuracy of interferometric measurements of a change in linear and angular displacement of an object. The apparatus and methods may also comprise measurement of intrinsic properties of the gas such as the reciprocal power of the gas.

In certain embodiments, the interferometric apparatus generates measurement of first and/or higher order spatial or temporal derivatives of effects of gas turbulence and acoustic perturbations on measured optical paths in interferometers. The first and/or higher order spatial or temporal derivatives of the effects can be integrated with respect to the corresponding spatial coordinate or inverted by a combination of Fourier transforms and inverse Fourier transforms to generate a contemporaneous measurement of gas turbulence and acoustic perturbation effects on measurements of linear and angular displacements by the interferometers. The contemporaneously measured values are used for compensating the gas turbulence and acoustic perturbation effects on the measurements of linear or angular displacements.

The effects of stationary non-random changes in the optical path length of measurement paths at the single wavelength of a non-dispersive interferometer can be compensated by using a procedure such as described in commonly owned U.S. patent application Ser. No. 10/294,158 entitled "COMPENSATION FOR EFFECTS OF VARIATIONS IN GAS REFRACTIVITY IN INTERFEROMETERS" by Henry A. Hill. The contents of the patent application are incorporated herein in their entirety by reference. The effects of stationary changes are compensated by using a procedure such as described in U.S. Provisional Patent Application No. 60/644,898 entitled "MULTI-AXIS INTERFEROMETER AND DATA PROCESSING FOR MIRROR MAPPING." Provisional Patent Application No. 60/644,898 is by Henry A. Hill and Gary Womack and the contents thereof are incorporated herein in their entirety by reference.

Planar encoder metrology systems are generally used herein in disclosed embodiments in the identification in situ of the effects of stationary non-random effects present in interferometric metrology systems.

In general, in a first aspect, the invention features a method, including conditioning a first input beam and a second input beam, forming a conditioned output beam from the conditioned first input beam and the conditioned second input beam, the conditioned output beam comprising a first interferometric phase including information about an optical path difference between the conditioned first input beam and the conditioned second input beam, deriving a first measurement beam and a first reference beam from the conditioned first input beam and conditioned second input beam, respectively, using an optical assembly and directing the first measurement beam to reflect from a measurement object remote from the optical assembly, wherein the conditioning causes the first measurement beam to be normally incident on the measurement object for a range of orientation angles of the measurement object with respect to the optical assembly, combining the first measurement beam and the first reference beam to form a first output beam including a second interferometric phase including information about an optical path difference between the first reference and measurement beams, detecting the conditioned output beam and the first output beam and monitoring the first and second interferometric phases based on the detected conditioned output beam and first output beam, respectively, monitoring a degree of freedom of the measurement object based the second interferometric phase, and reducing uncertainty in the monitored degree of freedom due to variations in the optical properties of a gas between the optical assembly and the measurement object based on the information from the first and second interferometric phases.

Implementations of the method can include one or more of the following features and/or features of other aspects. For example, conditioning the first input beam can include directing the first input beam to reflect from the measurement object. The first input beam can be directed to reflect from the measurement object twice. Conditioning the first input beam can cause the conditioned first input beam to be perpendicular to the measurement object for a range of orientation angles of the measurement object with respect to the optical assembly when it reflects from the measurement object the second time. Conditioning the first input beam can include directing the first input beam through an elliptical aperture.

In some embodiments, conditioning the second input beam includes directing the second input beam to reflect from the measurement object. The first input beam and the second input beam can be directed to reflect from the measurement object along parallel paths. The second input beam can be directed to reflect from the measurement object twice. The first input beam path on its first pass to the measurement object can be co-planar with the second input beam path on its second pass to the measurement object. The first input beam path on its second pass to the measurement object can be co-planar with the second input beam path on its first pass to the measurement object.

The first and second interferometric phases can include information about imperfections in a surface of the measurement object and reducing uncertainty comprises reducing uncertainty due to the imperfections based on the information from the first and second interferometric phases.

The first input beam and the second input beam can be derived from a common source.

The method can include flowing gas between the measurement object and the optical assembly. The gas can be flowed in a direction substantially perpendicular to the measurement beam path. The first and second input beams can be directed along corresponding paths to reflect a first time from the measurement object and the gas is flowed parallel to a plane defined the paths.

The first interferometric phase can include a term that is proportional to a spatial derivative of a term characterizing optical properties of the gas in the path of the first input beam between the optical assembly and the measurement object.

In certain embodiments, the method further includes deriving a second measurement beam and a second reference beam from the conditioned second input beam and conditioned first input beam, respectively, using the optical assembly and directing the second measurement beam to reflect from the measurement object, combining the second measurement beam and the second reference beam to form a second output beam including a third interferometric phase including information about an optical path difference between the second reference and second measurement beams, and detecting the second output beam and monitoring the third interferometric phase based on the detected second output beam, wherein the first and second input beams are derived from a common source. Reducing uncertainty in the monitored degree of freedom can include determining values of a first difference parameter from the second and third interferometric phases. The method can include determining information about a surface figure of the measurement object based on the values of the first difference parameter. Reducing uncertainty in the monitored degree of freedom can include inverting the values of the first difference parameter to obtain information about contributions of variations in the optical properties of the gas to the monitored interferometric phases of the first and second output beams. Inverting the values can include using a Fourier series or Fourier transform technique. A spacing between locations on the measurement object between the first and second measurement beams can be selected so that a region of low sensitivity of the Fourier series or Fourier transform technique corresponds to a frequency region where contributions of acoustic perturbations and turbulence to the monitored second and third interferometric phases is minimal.

In another aspect, the invention features a lithography method for use in fabricating integrated circuits on a wafer, the method including supporting the wafer on a moveable stage, imaging spatially patterned radiation onto the wafer, adjusting the position of the stage, and monitoring the position of the stage using the above-mentioned method, wherein the measurement object is attached to the stage and the position of the stage is monitored from the monitored degree of freedom of the measurement object with reduced uncertainty.

In a further aspect, the invention features a lithography method for fabricating integrated circuits on a wafer including positioning a first component of a lithography system relative to a second component of a lithography system to expose the wafer to spatially patterned radiation, and monitoring the position of the first component relative to the second component using the above-mentioned method, wherein the measurement object is attached to the first component and the position of the first component is monitored from the monitored degree of freedom of the measurement object with reduced uncertainty.

In general, in a further aspect, the invention features a method, including directing a first input beam and a second input beam to reflect from a measurement object, forming a first output beam from the first input beam after it reflects from the measurement object by combining the first input beam with the second beam, the first output beam including a first interferometric phase including information about an optical path difference between the first and second input beams, deriving a first measurement beam from the first input beam and deriving a first reference beam from the second input beam using an optical assembly and directing the first measurement beam to reflect from the measurement object, combining the first measurement beam and the first reference beam to form a second output beam including a second interferometric phase including information about an optical path difference between the first reference and measurement beams, detecting the first and second output beams and monitoring the first and second interferometric phases based on the detected output beams, monitoring a degree of freedom of the measurement object based the second interferometric phase, and reducing uncertainty in the monitored degree of freedom due to variations in the optical properties of a gas between the optical assembly and the measurement object based on the information from the first and second interferometric phases.

Implementations of the method can include one or more of the features discussed in relation to other aspects.

In general, in another aspect, the invention features a system, including a light source configured to produce a primary beam, a beam conditioning assembly configured to receive the primary beam, to derive a first input beam and a second input beam from the primary beam, to direct the first and second input beams to reflect from a measurement object at least once, and to output a first conditioned input beam and a second conditioned input beam, an interferometer assembly remote from the measurement object, the interferometer assembly being configured to receive the first and second conditioned input beams, to derive a first measurement beam from the first conditioned input beam and a first reference beam from the second conditioned input beam, to direct the first measurement and reference beams along different paths where the first measurement beam reflects from the measurement object, the interferometer assembly being further configured to combine the first measurement and reference beams to produce a first output beam including a first interferometric phase including information about a degree of freedom of the measurement object, a first detector configured to detect the first output beam, and an electronic processor in communication with the first detector, the electronic processor being configured to determine information about the degree of freedom of the measurement object based on the interference phase of at least one of the output beams and to reduce uncertainty in the degree of freedom due to variations in the optical properties of a gas between the interferometer assembly and the measurement object based on the first interferometric phase.

Embodiments of the system can include one or more of the following features and/or features of other aspects. For example, the beam conditioning assembly can be configured to direct the first and second input beams to reflect from the measurement object twice. For a range of orientation angles of the measurement object with respect to the interferometry assembly, the first and second input beams can be normally incident on the measurement object upon the second reflection from the measurement object.

The interferometer assembly can be configured to derive a second measurement beam from the second conditioned input beam and a second reference beam from the first conditioned input beam, to direct the second measurement and reference beams along different paths where the second measurement beam reflects from the measurement object, the interferometer assembly being further configured to combine the second measurement and reference beams to produce a second output beam including an interferometric phase including information about a second degree of freedom of the measurement object. The system can include a second detector configured to detect the second output beam, the second detector being in communication with the electronic processor. The paths of the first and second measurement beams can be parallel between the interferometer assembly and the measurement object. The beam conditioning assembly can be further configured to derive a conditioned output beam from each of the first and second conditioned input beams and to combine the two conditioned output beams to provide a combined conditioned output beam, the combined conditioned output beam including an interferometric phase including information about an optical path difference between the first conditioned input beam and the second conditioned input beam. The conditioned output beam can include a second interferometric phase including information about variations in the optical properties of a gas in the paths of the two conditioned input beams. The system can include a detector configured to detect the conditioned output beam, the detector being in communication with the electronic processor, wherein the electronic processor is configured to reduce uncertainty in the degree of freedom due to variations in the optical properties of a gas between the interferometer assembly and the measurement object based on the second interferometric phase.

The interferometry assembly can direct the first measurement beam to reflect from the measurement object only once. The beam conditioning assembly can be configured so that for a range of orientation angles of the measurement object with respect to the interferometry assembly, the first measurement beam is normally incident on the measurement object for the second reflection.

The measurement object can be a plane mirror measurement object. The measurement object can be attached to a wafer stage of a lithography tool. The interferometry assembly and beam conditioning assembly can be attached to frame of the lithography tool.

In another aspect, the invention features a lithography system for use in fabricating integrated circuits on a wafer, the system including an illumination system for imaging spatially patterned radiation onto the wafer, the above-mentioned system configured to monitor a position of the wafer relative to the imaged radiation, wherein wafer is supported by a moveable stage and the measurement object is attached to the stage; and a positioning system for adjusting the position of the stage relative to the imaged radiation. The lithography system can be a dual stage lithography system.

In another aspect, the invention features a lithography system for use in fabricating integrated circuits on a wafer, the system including an illumination system including a radiation source, a mask, a positioning system, a lens assembly, and the above-mentioned system, wherein during operation the source directs radiation through the mask to produce spatially patterned radiation, the positioning system adjusts the position of the mask relative to the radiation from the source, the lens assembly images the spatially patterned radiation onto the wafer supported by the stage, and the system monitors the position of the mask relative to the radiation from the source.

In general, in another aspect, the invention features a system, including a moveable stage configured to support a wafer and position the wafer relative to a projection lens, a first interferometer configured to direct a first measurement beam along a path between a first measurement object attached to the projection lens and a first interferometer assembly located remote from the projection lens, the first interferometer being configured to form a first output beam from the first measurement beam, the first output beam including a first interferometric phase including information about variations in an optical path length of the path between the first measurement object and the first interferometry assembly, a first detector configured to detect the first output beam, a second interferometer configured to direct a second measurement beam along a path between a second measurement object attached to the stage and a second interferometer assembly located remote from the stage, the second interferometer being configured to form a second output beam from the second measurement beam, the second output beam including a second interferometric phase including information about variations in an optical path length of the path between the second measurement object and the second interferometry assembly, a second detector configured to detect the second output beam, an electronic processor in communication with the first and second detectors, the electronic processor being configured to monitor a degree of freedom of the stage based on the second interferometric phase and to reduce uncertainty in the monitored degree of freedom due to variations in the optical properties in a gas in the path of the second measurement beam based on the first and second interferometric phases.

Embodiments of the system can include one or more of the following features and/or features of other aspects. For example, the first and second measurement beam paths can be in a path of a gas flow of gas introduced into an enclosure housing the stage. The first and second measurement beam paths can be parallel. The first measurement beam path can be sufficiently far from the stage so that gas turbulence due to movement of the stage does not cause substantial variations in the optical properties of the gas in the first measurement path.

The first interferometer can be a column reference interferometer. The second interferometer can be a multi-axis interferometer. The second interferometer can include a single pass interferometer. The second interferometer can include a plurality of single pass interferometers. The second interferometer can include a beam conditioning assembly.

The measurement object can be a plane mirror measurement object.

The system can include a third interferometer positioned remote from the stage, the third interferometer being a fixed measurement beam path interferometer where the measurement beam path is isolated from the gas in the second measurement beam path. The third interferometer can be positioned close to the second interferometer (e.g., sufficiently close so that adiabatic changes in the path of the measurement beam of the third interferometer are similar to the adiabatic changes in the path of the measurement beam of the second interferometer). The system can further include a third detector configured to detect a third output beam from the third interferometer, the third detector being in communication with the electronic processor and the electronic processor being configured to reduce uncertainty in the monitored degree of freedom due to variations in the optical properties of the gas based on the information in the third output beam. In some embodiments, the system includes a plurality of interferometers including the third interferometer, the plurality of interferometers being positioned at locations remote from the stage, each of the plurality interferometers being fixed measurement beam path interferometers where the measurement beam path of each is isolated from the gas in the second measurement beam path. The third interferometer can be a wavelength meter.

In certain embodiments, the system includes an optical encoder configured to monitor a degree of freedom of the stage.

In another aspect, the invention features a lithography system for use in fabricating integrated circuits on a wafer, the system including a projection lens for imaging spatially patterned radiation onto the wafer, the above-mentioned system for monitoring the position of the wafer relative to the imaged radiation, and a positioning system for adjusting the position of the stage relative to the imaged radiation, wherein the wafer is supported by the stage. The lithography system can be a dual stage lithography system.

In a further aspect, the invention features a lithography system for use in fabricating integrated circuits on a wafer, the system including an illumination system including a radiation source, a mask, a positioning system, a projection lens, and the above-mentioned system, wherein during operation the source directs radiation through the mask to produce spatially patterned radiation, the positioning system adjusts the position of the mask relative to the radiation from the source, the projection lens images the spatially patterned radiation onto the wafer supported by the stage, and the system monitors the position of the mask relative to the radiation from the source. The lithography system can be a dual stage lithography system. The lithography system can be an immersion lithography system.

In general, in a further aspect, the invention features an electronics module, including a first terminal configured to receive a signal from a column reference interferometer in a photolithography tool, a second terminal configured to receive a signal from a second interferometer configured to monitor a degree of freedom of a stage in the photolithography tool, and an electronics processor configured to monitor a degree of freedom of the stage based on the signal from the second interferometer and to reduce uncertainty in the monitored degree of freedom due to variations in the optical properties in a gas in a path of a measurement beam of the second interferometer based on the signals from the column reference interferometer and the second interferometer.

Embodiments may have one or more of the following advantages.

The systems and methods disclosed herein can provide accurate measurements of stage position and/or orientation in a lithography tool (e.g., a single or dual stage lithography tool). For example, the measurements can account for variations in the optical properties of a gas in a measurement beam path between the stage and interferometer as well as other sources of error, such as vibrations in the tool. As a result, measurements made using such interferometric metrology systems in a lithography tool can be compensated down to the sub-nanometer level.

The signal used in embodiments to compensate for variations in the optical properties of a gas (e.g., gas turbulence and acoustic perturbation effects) can be generated with zero data age.

Effects of first and higher order spatial derivatives of departures of the surface of the measurement object from a reference plane mirror surface can be measured in situ.

The "common mode" beam shear in the passive zero-shear interferometers at the input of the one or more interferometers can be approximately one to two orders of magnitude smaller than that present in a standard high stability plane mirror interferometer (HSPMI). The maximum common mode beam shear in the passive zero-shear interferometers can be 20 to 100 microns.

There can be reduced "differential mode" beam shear between the reference and measurement beams at a distance or angle measuring interferometer of a passive zero-shear interferometer. For example, there can be no differential mode beam shear between reference and measurement beams at a distance or angle measuring interferometer of a passive zero-shear interferometer for a range of positions of the measurement object relative the interferometer. The maximum differential mode beam shear in the input of the one or more interferometers can be less than or of the order of 5 microns.

There can be reduced differential mode beam shear (e.g., substantially no differential mode beam shear) between the reference and measurement beams at the detector of a passive zero-shear interferometer. The maximum differential mode beam shear at the detector can be less than or of the order of 5 microns. This feature can simplify fiber-optic pickup (FOP) vis-à-vis non-linear non-cyclic errors for use of both single mode and multi-mode fiber optics. This feature can also reduce (e.g., eliminate), by two or more orders of magnitude, the non-linear non-cyclic errors caused by beam shear and wavefront errors that are introduced by elements of the interferometer excluding the measurement object. The non-linear non-cyclic error caused a wavefront error introduced by the measurement object can be reduced by a factor of four or more depending upon the spatial properties of the wavefront error. Reduction of the differential mode beam shear in the passive zero-shear interferometer can permit use of smaller diameter beams in the presence of relatively large changes in orientation of the measurement object mirror. The reduction of the differential mode beam shear in the passive zero-shear interferometer can relax optical tolerances on interferometer and detector elements required to achieve a specified level of system performance.

The measurement beam in a passive zero-shear interferometer of the present invention can be always normal to the reflecting surface of a measurement object mirror, for at least a range of orientation angles of the measurement object mirror.

There can be no moving parts, i.e., no dynamic elements, in a passive zero-shear interferometer of the present invention.

The passive zero-shear interferometers can be configured to operate as single pass plane mirror interferometers. The corresponding passive zero-shear single pass plane mirror interferometer can have a reduced number of sources of cyclic error the same as with the dynamic interferometer such as described in commonly owned U.S. Pat. No. 6,563,593 B2 entitled "DYNAMIC ANGLE MEASURING INTERFEROMETER," No. 6,552,804 B2 entitled "APPARATUS AND METHOD FOR INTERFEROMETRIC MEASUREMENTS OF ANGULAR ORIENTATION AND DISTANCE TO A PLANE MIRROR OBJECT," and No. 6,917,432 entitled "INTERFEROMETERS FOR MEASURING CHANGES IN OPTICAL BEAM DIRECTION" all by Henry A. Hill. The contents of the three cited U.S. Patents are herein incorporated in their entirety by reference. Alternatively, the passive zero-shear interferometer can be configured to operate as a double pass plane mirror interferometer or as a multi-pass plane mirror interferometer where the number of passes is three or more.

Sub-harmonic cyclic errors present in multiple pass interferometers of the pitch-yaw-displacement section of a passive zero-shear interferometer can be eliminated as a result of separated beam paths.

The beam shear at the measurement object mirror in a passive zero-shear interferometer can be ¼ of the beam shear generated by the second pass beam to the measurement object mirror in a double pass plane mirror interferometer, e.g., a HSPMI.

The measurement object (e.g., measurement object mirror) can be smaller when using a passive zero-shear interferometer. Similarly, the interferometer components in the passive zero-shear interferometer can be smaller relative to comparable systems.

The interference signal amplitude in a passive zero-shear interferometer of the present invention can be independent of pitch and yaw. This feature can improve efficiency of the interferometer system with respect to laser beam intensity by a factor of about 2 to 3. The factor may be even larger when considering properties of a standard HSPMI in the context of a large maximum beam shear such as 4 mm.

A passive zero-shear single pass plane mirror interferometer can be used with passive angle interferometers, i.e., angle detectors that have no moving parts. Examples of passive angle interferometers are those developed for the dynamic interferometer to measure pitch, yaw, and displacement based on a single measurement beam contacting the measurement object mirror (see referenced U.S. Pat. No. 6,563,593 B2, U.S. Pat. No. 6,552,804 B2, and U.S. Pat. No. 6,917,432).

Certain of the surface properties of measurement object mirrors can be characterized in-situ in a litho-tool configured with a metrology system based on passive zero-shear single pass plane mirror interferometers and no additional reference flats are required.

The passive zero-shear interferometer can be placed on a moving stage with the measurement object mirrors located off the stage.

In some embodiments, a passive zero-shear interferometer can be aligned at the factory with no additional alignment of the passive zero-shear interferometer required in the field.

The passive zero-shear feature of the passive zero-shear interferometers cited with respect to a zero relative shear of output reference and measurement beams can also mean that portions of the input reference and measurement beams conjugate to the reference and measurement output beams, respectively, exhibit no lateral shear (this is not necessarily the case for example with a HSPMI used with a measurement object mirror that experiences changes in orientation).

Another advantage of disclosed embodiments is that a metrology system including an interferometer metrology system and a planar encoder metrology system reduces the requirements placed on the encoder system, e.g., the encoder system does not have to handle a set of redundancy problems or the spatial patterns on the encoder scales may be a simple two dimensional grating.

Another advantage is that a planar encoder metrology system of a metrology system including an interferometer metrology system and the encoder metrology system does not have to include absolute planar encoders.

Another advantage is that the measurement of stationary non-random effects of gas in a metrology system including an interferometer metrology system and a planar encoder metrology system is performed in situ.

Another advantage of disclosed embodiments is a compensation for effects of mechanical resonances and vibrations that are detected with different efficiencies in, for example, column reference interferometers in a lithography tool, interferometer metrology systems that measure and monitor the position of a stage of the lithography tool, and an interferometer used to measure and monitor adiabatic changes in the gas of the lithography tool.

Another advantage is a compensation for adiabatic effects wherein data relating to measurement and monitoring of the adiabatic effects is not segmented or fragmented by the exchange of stages or wafer chucks in dual stage lithography tools, i.e., a reduced initialization problem.

Another advantage is a compensation for non-adiabatic isotropic effects, e.g., such as measured by a column reference interferometer, wherein data relating to measurement and monitoring of the non-adiabatic isotropic effects is not segmented or fragmented with the exchange of stages or wafer chucks in dual stage lithography tools, i.e., a reduced initialization problem.

Another advantage is a compensation for non-adiabatic isotropic effects wherein the non-adiabatic isotropic effects, e.g., such as measured by a column reference interferometer, are scalable to match optical path lengths of other interferometers of an interferometer metrology system.

Another advantage is a compensation for non-adiabatic non-isotropic effects wherein data relating to measurement and monitoring of the non-adiabatic non-isotropic effects may be segmented or fragmented with the exchange of stages or wafer chucks in dual stage lithography tools by the exchange of stages or wafer chucks or may not be segmented or fragmented in a single stage lithography tool.

Another advantage is a compensation for effects of gas composition changes due to exposure of a wafer in a non-immersion or an immersion lithography tool wherein the effects of composition changes are treated as stationary non-random effects.

Another advantage is a compensation for low order gradients in non-adiabatic effects in interferometer metrology systems with the use of two or more interferometers (e.g., LRI's) that measure and monitor adiabatic changes in the gas of a lithography tool.

Another advantage is an initialization for stationary effects in interferometer metrology systems wherein data relating to measurement and monitoring of the non-adiabatic non-isotropic effects are segmented or fragmented by the exchange of stages or wafer chucks in dual stage lithography tools.

Another advantage is that sections of planar encoders used in planar encoder metrology systems for measurement and monitoring of stationary effects may be located on a wafer chuck.

Another advantage is that sections of planar encoders used in planar encoder metrology systems for measurement and monitoring of stationary effects may be located in the kerfs of in process wafers.

Another advantage is that stationary effects in column reference interferometers, e.g., such as generated by body deformation from stage motion and body deformation from thermal drift, are measured and monitored.

Another advantage is that stationary non-random effects of gas can be incorporated in the initialization of an interferometer metrology system associated with the exchange of a stage or wafer chuck.

The details of one or more embodiments are set forth in the accompanying drawings and the description below. Other features and advantages will be apparent from the description and drawings.

BRIEF DESCRIPTION OF DRAWINGS

The structure and operation of embodiments disclosed herein may best be understood by reading the detailed description in conjunction with the drawings wherein disclosed embodiments' parts have assigned reference numerals that are used to identify them in all of the drawings in which they appear and wherein:

FIG. 2b is a diagram of the measurement beam spots on a measurement object of the interferometer system shown in FIG. 2a.

FIG. 3b is a diagram of the measurement/reference beam spots on a measurement object of the interferometer system shown in FIGS. 2a and 3a.

Like reference symbols in the various drawings indicate like elements.

DETAILED DESCRIPTION

Figure 1:
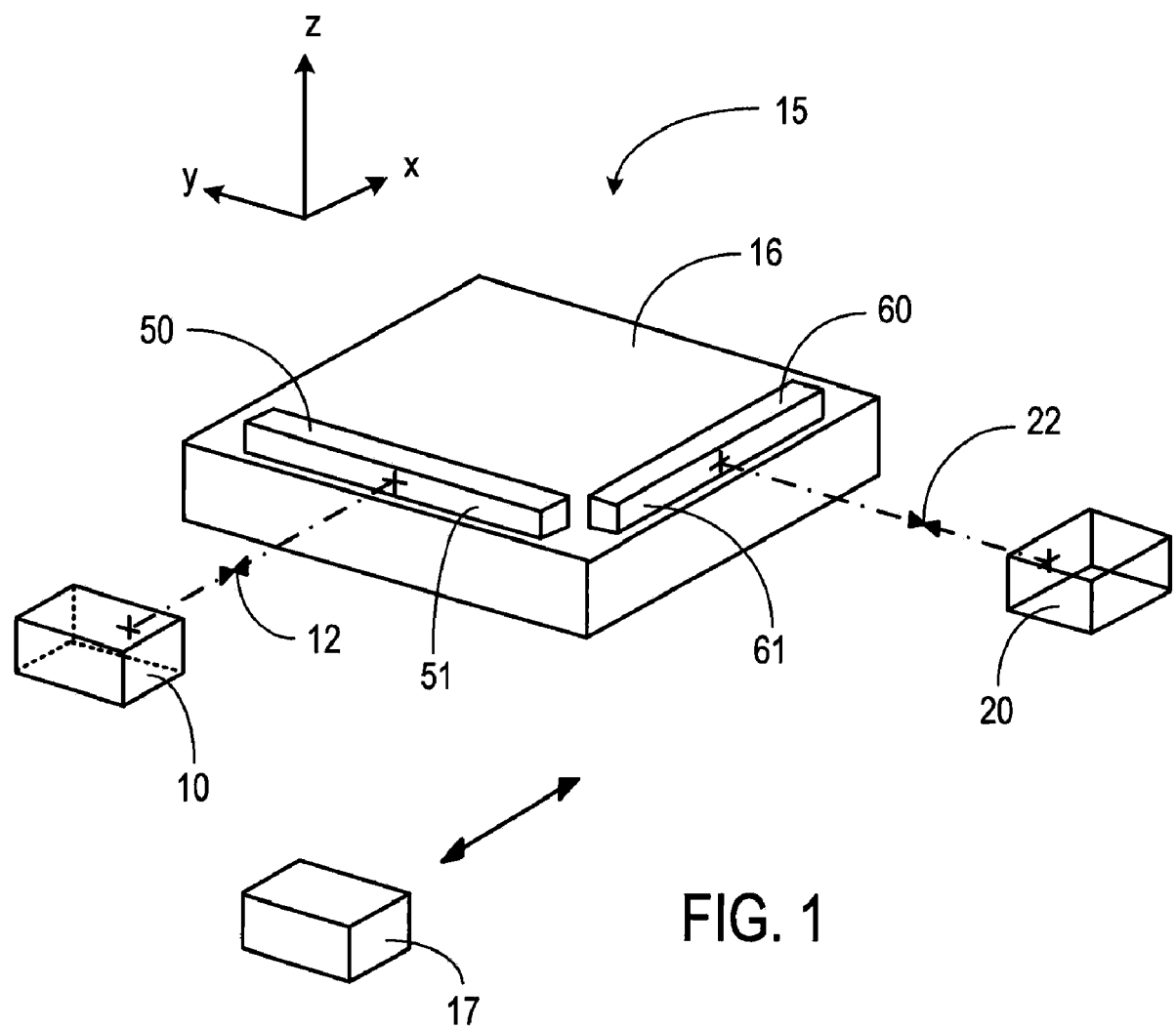
FIG. 1 is a schematic perspective view of an interferometer system that monitors the position of an object and compensates for effects of the optical properties of a gas in the measurement and/or reference paths of the interferometer system.

Reference is made to FIG. 1 which is a diagrammatic perspective view of an interferometric system 15 that employs a pair of orthogonally arranged interferometers or interferometer subsystems by which the location and orientation of on-stage mounted stage mirrors may be measured in situ with high spatial resolution along one or more datum lines and by which effects of a dispersive medium such as a gas in the measurement and/or reference beam paths may be compensated. As shown in FIG. 1, system 15 comprises a stage 16 that forms part of a photolithographic apparatus for fabricating semiconductor products such as integrated circuits or chips. Affixed to stage 16 is a plane stage mirror 50 having a y-z reflective surface 51 elongated in the y-direction.

Also, fixedly mounted to stage 16 is another plane stage mirror 60 having an x-z reflective surface 61 elongated in the x-direction. Mirrors 50 and 60 are mounted on stage 16 so that their reflective surfaces, 51 and 61, respectively, are nominally orthogonal to one another. Stage 16 is otherwise mounted for nominally plane translation but may experience small angular rotations about the x, y, and z axes due to bearing and drive mechanism tolerances. In normal operation, system 15 is adapted to be operated for scanning in the y-direction for set values of x.

Fixedly mounted off-stage is an interferometer (or interferometer subsystem) that is generally indicated at 10. The purpose of interferometer 10 generally is to measure using non-dispersive interferometry a FDP of reflecting surface 51 and of the gas in the measurement beam paths of interferometer 10 and to measure the position of stage 16 in the x-direction and the angular rotations of stage 16 about the y- and z-axes as stage 16 translates in the x- and y-direction. Interferometer 10 comprises plane interferometers such as interferometer 100 shown in FIG. 2a and arranged so that interferometric beams travel to and from mirror 50 generally along an optical path designated as 12.

Also fixedly mounted off-stage is an interferometer (or interferometer subsystem) that is generally indicated at 20. The purpose of interferometer 20 generally is to measure using non-dispersive interferometry a FDP of reflecting surface 61 and of the gas in the measurement beam paths of interferometer 20, the position of stage 16 in the y-direction, and the angular rotations of stage 16 about the x- and z-axes as stage 16 translates in the x- and y-direction in addition to other information such as used in mapping surface 61 of mirror 60. Interferometer 20 comprises plane interferometers such as interferometer 100 shown in FIG. 2a and arranged so that interferometric beams travel to and from mirror 60 generally along an optical path designated as 22.

The signals from interferometers 10 and 20 are processed by electronic processor 17.

In embodiments of the present invention, interferometer subsystems 10 and 20 may comprise apparatus and methods of non-dispersive interferometry in combination for the compensation of effects of a dispersive medium such as a gas in the measurement and/or reference beam paths of the respective interferometer subsystems 10 and 20. Interferometer subsystems 10 and 20 may comprise a refractometer/wavelength monitor or monitors.

Embodiments relate to apparatus and methods by which a change in a measurement and or reference beam path may be quickly measured and used in contemporaneous applications or in non-contemporaneous applications wherein either or both the optical properties of a gas in the measurement path and/or the physical length of the measurement path may be changing. An example of a contemporaneous application is in an interferometric angle and/or distance measuring instrument to enhance accuracy by compensating for gas turbulence and acoustic perturbation effects on the optical properties of the gas in the measurement and/or reference beam paths, especially changes in the measurement and reference beam paths that take place during the measuring period because of gas turbulence and acoustic perturbation effects induced in the measurement and reference beam paths by rapid stage slew rates. An example of a non-contemporaneous application is an interferometric angle and/or linear displacement measuring instrument to enhance accuracy of compensating for gas turbulence and acoustic perturbation effects in determination of alignment mark locations.

Non-dispersive interferometry used for the compensation of certain of the effects of a gas in the measurement and/or reference beam paths is based on interferometric measurements using measurement beams including a single optical wavelength. The non-dispersive techniques are based on the measurement of effects of the gas on the optical path length experienced by a beam.

Figure 2A:
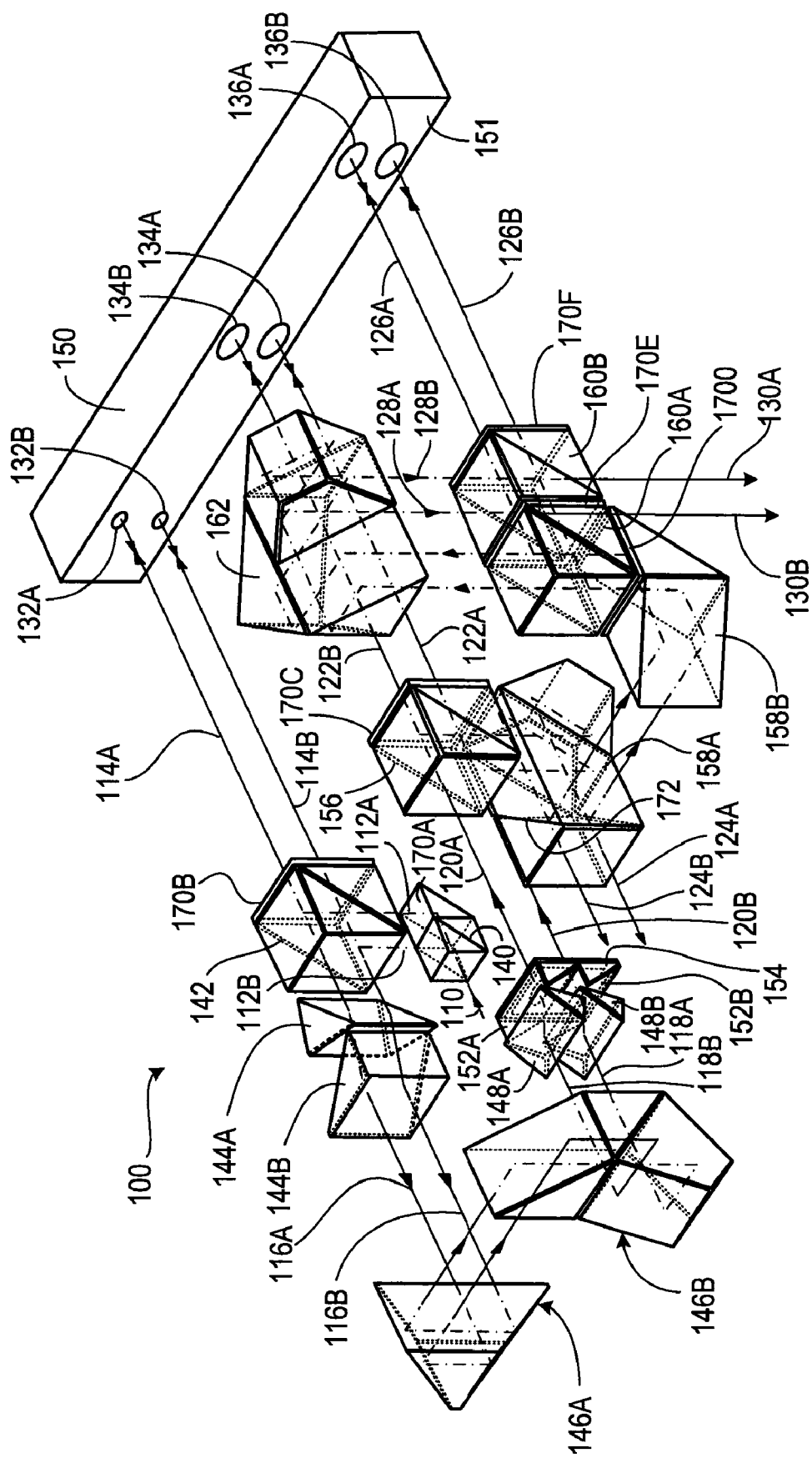
FIG. 2a is an exploded perspective view of an interferometer system that compensates for turbulence and acoustic perturbation effects of gas in a measurement or reference beam path.

FIG. 2a shows an embodiment of a multiple measurement beam paths plane mirror interferometer 100 that measures the effects of the gas on the optical path length experienced by a beam. The interferometer directs multiple measurement beams to each contact a measurement object 120 three or more times. For example, the measurement object may be a stage mirror for a wafer stage in a microlithography system. Interferometer 100 produces multiple output beams 124A, 124B, 130A, and 130B each including interferometric information about changes in distance between the interferometry system and the measurement object along a corresponding measurement axis, changes in orientation of the measurement object, and effects of turbulence and acoustic perturbations on the multiple output beams.

Interferometer 100 has the property that the output beams each includes a measurement component that makes at least two passes to the measurement object before being detected or before being directed along separate measurement beam paths for a third pass to the measurement object. Accordingly, the interferometer is similar to those disclosed in commonly owned U.S. Pat. No. 6,819,434 B2 by Henry, A. Hill and entitled "Multiple Degree Of Freedom Interferometer." The contents of U.S. Pat. No. 6,819,434 B2 are incorporated herein in their entirety by reference. Interferometer 100 is different from those disclosed in the referenced patent in that it provides two interferometric signals for each of one or more measurement axes, a feature that can be used to provide gas turbulence and acoustic perturbation information for respective measurement beam paths and surface information about the measurement object independent of its angular orientation.

Interferometer 100 is also different from those disclosed in commonly owned U.S. Pat. No. 6,757,066 entitled "Multiple Degree Of Freedom High Stability Plane Mirror Interferometer;" U.S. Provisional Patent Applications No. 60/534,481 entitled "Multi-Axis Interferometer For Mirror Mapping," No. 60/535,078 entitled "Multi-Axis Interferometer For Mirror Mapping," No. 60/564,448 entitled "Multi-Axis Interferometer And Data Processing For Mirror Mapping," and No. 60/644,898 entitled "Multi-Axis Interferometer And Data Processing For Mirror Mapping;" and U.S. patent application Ser. No. 11/030,755 entitled "Multi-Axis Interferometer For Mirror Mapping," Ser. No. 11/112,375 entitled "Multi-Axis Interferometer And Data Processing For Mirror Mapping," and Ser. No. 11/112,681 entitled "Multi-Axis Interferometer And Data Processing For Mirror Mapping." The provisional applications No. 60/564,448 and No. 60/644,898 and the utility application Ser. No. 11/112,375 and Ser. No. 11/112,681 are by Henry A. Hill and Gary Womack and the remaining cited patent, provisional applications, and utility applications are by Henry A. Hill. The contents of the cited patent, provisional applications, and the utility applications are hereby incorporated herein in their entirety by reference. The interferometers described in cited patent, provisional applications, and the utility applications are different from interferometer 100 in that they provide three measurement axes in a common plane and the first pass measurement beam for each of the three axes is a common beam.

In the described embodiment, interferometer 100 includes a beam conditioning section and two single pass plane mirror interferometers wherein the measurement axes of the two single pass plane mirror interferometers are parallel and lie in a common vertical plane. The two single pass plane mirror interferometers comprise polarizing beam-splitters 160A and 160B, half-wave phase retardation plates 170D and 170E, retroreflector 162, and quarter-wave phase retardation plate 170F. The two output beams from the two single pass plane mirror interferometers are 130A and 130B. The beam conditioning section comprises polarizing beam-splitters 142 and 156; afocal systems including anamorphic prisms 144A, 144B, 148A, 148B, 152A, and 152B; a retroreflector including elements 146A and 146B, and aperture mask 154.

There are six measurement beams that contact measurement object 150 at spots 132A, 134A, and 136A and at spots 132B, 134B, and 136B. The measurement beams associated with elliptical spots 132A, 134A, and 136A are derived from input beam component 112A and measurement beam spots 132B, 134B, and 136B are derived from input beam 112B. The design of the beam conditioning in the vertical direction in interferometer 100 is such that spots 132A, 134B, and 136A lie in one horizontal line and spots 132B, 134A, and 136B lie is a second horizontal line. This is achieved in interferometer 100 with optical elements as shown in FIG. 2a and an additional Rhomb (not shown in FIG. 2a) placed to introduce a vertical displacement of beams, e.g., placed in the paths of beams 116A and 116B, in the paths of beams 118A and 118B, or between the set anamorphic prism elements 152A and 152B and aperture mask 154. The vertical separation between the top row of spots 132A, 134B, and 136A and the bottom row of spots 132B, 134A, and 136B is b (see FIG. 2b). b may be relatively small (e.g., on the order of one or two centimeters), allowing a relatively narrow mirror to be used for plane stage mirror 50. In the described embodiment, the six spots are arranged in three vertical columns. However, the six spots may be arranged in some other geometric pattern depending on, for example, expected gas flow or stage mirror shape in the system. The shape of spots 132A, 134A, and 136A and spots 132B, 134B, and 136B are elliptical in cross-section so as to minimize the effects of beam shears introduced by changes in orientation of measurement object 150.

Continuing with the description, interferometer 100 includes a polarizing beam splitter 140 which splits an input beam 110 including two orthogonally polarized components with a difference in frequencies of $\omega_R$ into first and second measurement components 112A and 112B, respectively. Interferometer 100 also includes half-wave phase retardation plate 170A which rotates the plane of polarization of measurement beam 112A by 90° such that first and second measurement beams 112A and 112B are in the same polarization state. First and second measurement beams 112A and 112B are reflected by polarizing beam splitter 142 as first and second measurement beams 114A and 114B, respectively. Interferometer 100 directs first and second measurement beams 114A and 114B along paths that contact measurement object 150 at different locations in a vertical or z direction at spots 132A and 132B, respectively.

Interferometer 100 also includes quarter-wave phase retardation plate 170B which is located between polarizing beam splitter 142 and measurement object 150. Quarter-wave phase retardation plate 170B rotates by 90° the polarization states of double passed beams directed between the polarizing beam splitter 142 and measurement object 150. Accordingly, polarizing beam splitter 170B transmits an out-going beam that would have been reflected in its incoming polarization state.

The direction of propagation of components of measurement beams 114A and 114B reflected by measurement object 150 is changed by pitch and yaw angles $2\theta_P$ and $2\theta_Y$ for a change in orientation of measurement object 150 by pitch and yaw angles $\theta_P$ and $\theta_Y$, respectively. Measurement beams 114A and 114B reflected by measurement object 150 are next transmitted by polarizing beam-splitter 142 and anamorphic prisms 144A and 144B as yaw expanded measurement beams 116A and 116B, respectively. The magnification $\eta_Y$ in the yaw plane is selected such that $$\eta_Y = 2. \tag{1}$$

Accordingly, the direction of propagation $\theta'_Y$ of measurement beams 116A and 116B in the yaw direction is $$\vartheta'_Y = \left(\frac{2}{\eta_Y}\right)\vartheta_Y \tag{2}$$
$$= \vartheta_Y.$$

Yaw expanded measurement beams 116A and 116B are next reflected as yaw expanded measurement beams 118B and 118A, respectively, by a retroreflector including elements 146A and 146B. Retroreflector including elements 146A and 146B is shown in FIG. 2a as a polarization preserving retroreflector such as described in U.S. Pat. No. 6,198,574 B1 entitled "Polarization Preserving Optical Systems" and No. 6,201,609 B1 entitled "Interferometers Utilizing Polarization Preserving Optical Systems." Both of the two cited patents are by Henry A. Hill and the contents thereof are incorporated in their entirety by reference. Other types of retroreflectors may be used in embodiments of the present invention, e.g., a corner cube retroreflector, without departing from the scope and spirit of the present invention. Retroreflectors 146A and 146B can invert the positions of beams 116A and 116B with respect to the z-axis.

Yaw expanded measurement beams 118B and 118A are next expanded in the pitch direction as pitch and yaw expanded measurement beams corresponding to beams 120B and 120A, respectively, by anamorphic prisms 148A and 148B and anamorphic prisms 152A and 152B. The magnification $\eta_P$ in the pitch plane is selected such that $$\eta_P = 2. \quad (3)$$

Accordingly, the direction of propagation $\theta'_P$ of expanded measurement beams corresponding to beams 120B and 120A in the pitch direction is $$\vartheta'_P = \left(\frac{2}{\eta_P}\right)\vartheta_P \quad (4)$$
$$= \vartheta_P.$$

As a consequence of the conditions set out in Eqs. (2) and (4), the direction of propagation of expanded measurement beams corresponding to beams 120B and 120A are always perpendicular to the surface of plane measurement object 150 independent of changes in orientation of measurement object 150.

The expanded measurement beams 120B and 120A correspond to portions of corresponding expanded measurement beams transmitted by anamorphic prisms 152A and 152B, respectively. Aperture mask 154 comprises to two apertures that are elliptical in cross-section to generate the elliptical cross-sectional shape of spots 134B, 134A, 136A, and 136B and the demagnified elliptical cross-sectional shape of conjugate image spots 132A and 132B. As a result of aperture mask 154, there is no beam shear of measurement beams 120B and 120A at aperture mask 154.

In the last step of the beam conditioning section of interferometer 100, measurement beams 120B and 120A each make a single pass to measurement object 150 as measurement beams 122B and 122A, respectively, to form spots 134B and 134A, respectively. Components of measurement beams 122B and 122A are incident on measurement object 150 with zero values for respective angles of incidence.

The pitch and yaw beam shears $s_{P,2}$ and $s_{Y,2}$, respectively, of measurement beams 122B and 122A at spots 134B and 134A are given by the formula $$s_{P,2} = \theta_P L,$$
$$s_{Y,2} = \theta_Y L \quad (5)$$

where L is the one way physical path length of measurement beams 122B and 122A. Note that the beam shears expressed by Eq. (5) is ¼ of the corresponding beam shears experienced in for example a HSPMI.

The respective components of beams 122B and 122A are parallel because of the zero angle of incidence of components of beams 122B and 122A at measurement object 150. The components of beams 122B and 122A incident on polarizing beam-splitter 156 are reflected as a result of the double pass through quarter-wave phase retardation plate 170C. The reflected components of beams 122B and 122A are incident on a retroreflector including elements 158A and 158B. The description of retroreflector including elements 158A and 158B is the same as the description given for retroreflector including elements 146A and 146B.

A first portions of reflected components of beams 122B and 122A incident on the retroreflector including elements 158A and 158B are transmitted by non-polarizing beam-splitter 172 as beams 124A and 124B, respectively. Beams 124A and 124B are subsequently combined as a mixed beam and detected to generate the first electrical interference signal $S_1$.

The frequency domains of the stationary non-random effects of a gas and other gas related effects generally fall into separated regions. For turbulence effects, the corresponding frequency domain is generally determined by dimensions of turbulent cells and the speed of transport of the cells through the measurement and/or reference beam paths. For the example of a turbulence generated cell with a characteristic dimension of 0.04 m and an gas flow speed perpendicular to the axes of the measurement and/or reference beam paths of 0.2 m/s, the corresponding frequency is of the order of 5 Hz.

The frequency domain of stationary non-random effects is determined by the frequency spectrum of velocity profile of a scanning stage. A characteristic frequency of the frequency spectrum is the inverse of the time to scan a single die site on a wafer, e.g., 10 Hz.

The frequency domain of vibrations is determined by the resonant frequencies of different components of a lithographic tool including the metrology system used to measure the position of the respective stage.

The frequency domain of an acoustic perturbation except for an acoustic pulse generated by an acceleration of a measurement object will be determined primarily by the normal mode spectrum of a cavity containing interferometer system 15. For the example of interferometer system 15 located in a lithography tool with characteristic dimensions of 1.5 m, the normal mode spectrum of the lithography tool will comprise a fundamental mode with a frequency of approximately 200 Hz and harmonic modes thereof. Environmental effects of the gas generally generate changes in the optical path lengths with frequencies approximately 1 Hz.

The phase $\Phi_1$ of electrical interference signal $S_1$ is independent of linear displacements of measurement object 150, is sensitive to angular displacements in pitch of measurement object 150, is sensitive to gas turbulence and acoustic perturbation effects in second and higher order spatial derivatives, and is sensitive to second and higher order spatial derivatives of the surface figure of measurement object 150 as expressed by the following equation, $$\Phi_1 = k\left\{b\vartheta_P + 4\left(\frac{b}{2}\right)\left(\frac{c}{2}\right)\left(\frac{\partial}{\partial x}\frac{\partial}{\partial z}\right)(\zeta_{1,2} + \xi_{1,2})\right\} \quad (6)$$

where k is the wavenumber of the respective measurement beams; c is the horizontal spacing of spots 132A, 132B, 134B, and 134A; $\zeta_{1,2}$ represents the effects of gas turbulence and acoustic perturbations along an axis defined by measurement beams 114A, 114B, 122B, and 122A; and $\xi_{1,2}$ represents the effects of surface figure errors of measurement object 150 at a spot defined by the location of spots 132A, 132B, 134B, and 134A. Note that there are no first order spatial derivatives of $\zeta_{1,2}$ and $\xi_{1,2}$ present in Eq. (6) as a result of the design of interferometer 100 that places spots 132A and 134B in one horizontal line and spots 132B and 134A in a second horizontal line.

It is evident on examination of Eq. (6) that a measurement of the change in pitch of measurement object 150 is obtained from measurements of $\Phi_1$ that is compensated for effects of gas turbulence and acoustic perturbation effects up through first order spatial derivatives of the gas turbulence and acoustic perturbation effects. It is also evident on examination of Eq. (6) that a measurement of the change in pitch of measurement object 150 is obtained from measurements of $\Phi_1$ that is compensated for effects errors in the surface figure of measurement object 150 up through first order spatial derivatives of the surface figure errors.

A second portions of reflected components of beams 122B and 122A incident on the retroreflector including elements 158A and 158B are reflected by non-polarizing beam-splitter 172 as measurement beams incident on half-wave phase retardation plate 170D. Half-wave phase retardation plate 170D is oriented so as to rotate the plane of polarizations of the second portions of reflected components of beams 122B and 122A by 45°.

A first portions of the second portions of reflected components of beams 122B and 122A are transmitted by polarizing beam-splitter 160A and a retroreflector 162 as reference beams 128A and 128B. The description of retroreflector 162 is the same as the description given for the retroreflector including elements 146A and 146B. A second portions of the second portions of reflected components of beams 122B and 122A are reflected by polarizing beam-splitter 160A and transmitted by polarizing beam-splitter 160B as measurement beams 126A and 126B. Measurement beams 126A and 126B are transmitted by polarizing beam-splitter 160B as a result of passing through half-wave phase retardation plate 170E which is oriented so as to rotate the plane of polarization of the respective beams by 90°.

The shear of reference beams 128A and 128B and measurement beams 126A and 126B at polarizing beam-splitter 160B is reduced because of the short path length between beam-splitter 160B and aperture mask 154 and because of the reduced magnitude of the changes in the directions of propagation of the respective beams. The shear of measurement beams 126A and 126B at measurement object 150 is the same as given by Eq. (5). Note again that the beam shears for measurement beams 126A and 126B at measurement object 150 is ¼ of the corresponding beam shears experienced in for example a HSPMI.

The components of measurement beams 126A and 126B incident on polarizing beam-splitter 160B are reflected after a double pass through quarter-wave phase retardation plate 170F as measurement beam components of output beams 130A and 130B, respectively. Reference beams 128A and 128B are transmitted by polarizing beam-splitter 160B as reference beam components of output beams 130B and 130A, respectively. The components of output beams 130A and 130B are subsequently mixed and detected as electrical interference signals $S_5$ and $S_6$, respectively.

The phases $\Phi_5$ and $\Phi_6$ of electrical interference signals $S_5$ and $S_6$, respectively, contain information about the displacement of measurement object 150, about the effects of gas turbulence and acoustic perturbation effects, and about errors in the surface figure of measurement object 150 according to the following equations.

$$\Phi_5 = 2k(L+\zeta_5+\xi_5)+kb\theta_P, \quad (7)$$

$$\Phi_6 = 2k(L+\zeta_6+\xi_6)-kb\theta_P \quad (8)$$

where $\zeta_5$ and $\zeta_6$ represents the effects of gas turbulence and acoustic perturbations along the paths of measurement beams 126A and 126B, respectively, and $\xi_5$ and $\xi_6$ represents the effects of surface figure errors of measurement object 150 at the location of spots 136A and 136B, respectively.

The difference in phases $\Phi_5-\Phi_6$ is next computed to generate a first difference parameter (FDP), $$\Phi_5-\Phi_6 = 2kb\theta_P+k(\zeta_5-\zeta_6)+(\xi_5-\xi_6). \quad (9)$$

The average of $\Phi_5-\Phi_6$ is used to obtain information in situ about the effects of surface figure errors of measurement object 150 at the location of spots 136A and 136B, respectively. The phase difference $\Phi_5-\Phi_6$ compensated for the measured effects of surface figure errors of measurement object 150 and compensated for changes in pitch using the results of measured values of $\Phi_1$ are inverted to obtain a value for the average value of $(\zeta_5+\zeta_6)$. The average value of $(\zeta_5+\zeta_6)$ is subsequently used to compensate for effects of gas turbulence and acoustic perturbation effects in the measured value of the displacement of measurement object 150 from the sum $(\Phi_5+\Phi_6)$.

Figure 3A:
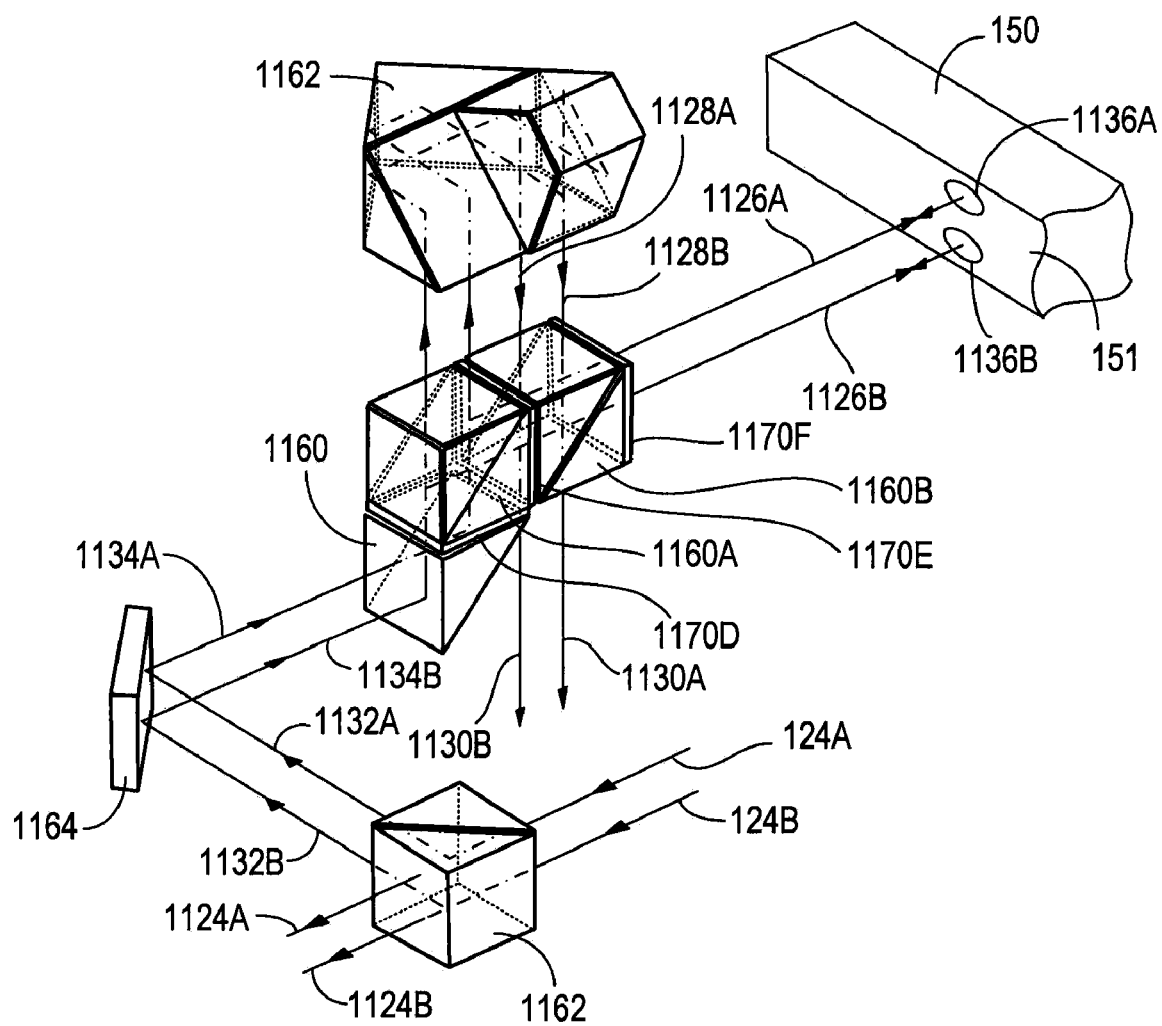
FIG. 3a is an exploded perspective view of another section of a multi-axis plane mirror interferometer system including the first section of the multi-axis interferometer system shown in FIG. 2a that measures and monitors the effects of other related effects of gas, e.g., turbulence and acoustic effects, in a lithography tool.

While interferometer 100 as shown in FIG. 2a is a three degree-of-freedom interferometer, other configurations are also possible. For example, in some embodiments, interferometer 100 can be configured as a five-axis interferometer. Referring to FIG. 3a, interferometer 100 can include a second set of the two single pass plane mirror interferometers. The second set of interferometers include polarizing beam-splitters 1160A and 1160B, half-wave phase retardation plates 1170D and 1170E, retroreflector 1162, and quarter-wave phase retardation plate 1170F. The two output beams from the second set of two single pass plane mirror interferometers are 1130A and 1130B.

Figure 3B:
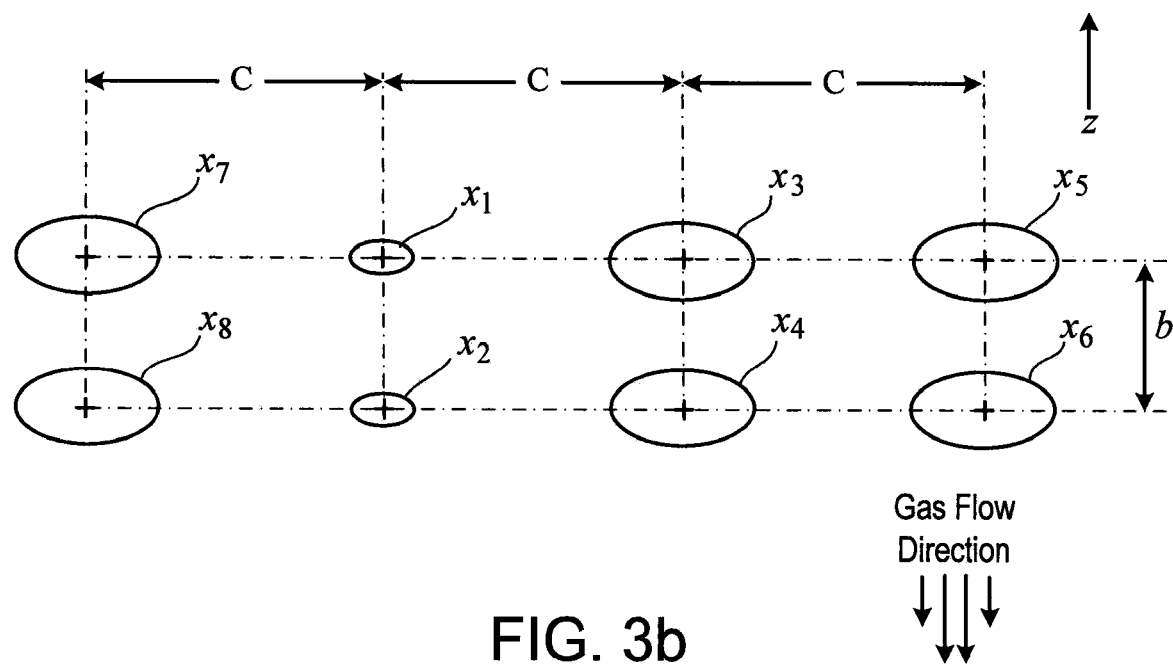

Accordingly, and with reference to FIG. 3b, there are eight measurement/reference beams that contact measurement/reference object 150 at spots 132A, 134A, 136A, and 1136A and at spots 132B, 134B, 136B, and 1136B. The measurement/reference beams associated with spots 132A, 134A, 136A, and 1136A are derived from input beam component 112A and measurement/reference beam spots 132B, 134B, 136B, and 1136B are derived from input beam 112B. The vertical separation between the top row of spots 132A, 134B, 136A, and 1136A and the bottom row of spots 132B, 134A, 136B, and 136B is b. In the described embodiment, the eight spots are arranged in four vertical columns. However, the eight spots may be arranged in some other geometric pattern without departing from the scope and spirit of the present disclosure.

The shape of spots 132A, 134A, 136A, and 1136A and spots 132B, 134B, 136B, and 1136B are elliptical in cross-section so as to minimize the effects of beam shears introduced by changes in orientation of measurement object 150 about the y direction (coordinate system used in FIG. 3b).

For the second set of the two single pass interferometers, a second portions of beams 124A and 124B are reflected by non-polarizing beam-splitter 1162 as beams 1132A and 1132B, respectively, and beams 1132A and 1132B are subsequently reflected by mirror 1164 as beams 1134A and 1134B, respectively.

Beams 1124A and 1124B are mixed and detected as discussed for beams 124A and 124B above.

Beams 1134A and 1134B are reflected by prism 1166 as measurement beams incident on half-wave phase retardation plate 1170D. Half-wave phase retardation plate 1170D is oriented so as to rotate the plane of polarizations of the second portions of reflected components of beams 122B and 122A by 45°. A first portions of the beams incident on half-wave phase retardation plate 1170D are transmitted by polarizing beam-splitter 1160A and a retroreflector 1162 as reference beams 1128A and 1128B, respectively. The description of retroreflector 1162 is the same as the description given for the retroreflector including elements 146A and 146B. A second portions of the beams incident on half-wave phase retardation plate 1170D are reflected by polarizing beam-splitter 1160A and transmitted by polarizing beam-splitter 1160B as measurement beams 1126A and 1126B, respectively. Measurement beams 1126A and 1126B are transmitted by polarizing beam-splitter 1160B as a result of passing through half-wave phase retardation plate 170E which is oriented so as to rotate the plane of polarization of the respective beams by 90°.

The shear of reference beams 1128A and 1128B and measurement beams 1126A and 1126B at polarizing beam-splitter 1160B is reduced because of the short path length between beam-splitter 1160B and aperture mask 154 and because of the reduced magnitude of the changes in the directions of propagation of the respective beams. The shear of measurement beams 1126A and 1126B at measurement object 150 is the same as given by Eq. (5). Note again that the beam shears for measurement beams 1126A and 1126B at measurement object 150 is ¼ of the corresponding beam shears experienced in for example a HSPMI.

The components of measurement beams 1126A and 1126B incident on polarizing beam-splitter 1160B are reflected after a double pass through quarter-wave phase retardation plate 1170F as measurement beam components of output beams 1130A and 1130B, respectively. Reference beams 1128A and 1128B are transmitted by polarizing beam-splitter 1160B as reference beam components of output beams 1130B and 1130A, respectively. The components of output beams 1130A and 1130B are subsequently mixed and detected as electrical interference signals $S_7$ and $S_8$, respectively. The detectors include analyzers to mix polarization components of output beams Phases $\Phi_7$ and $\Phi_8$ of electrical interference signals $S_7$ and $S_8$, respectively, contain information about the displacement of measurement object 150; about the stationary non-random effects of the gas and the other related effects of the gas along measurement paths $x_7$ and $x_8$, respectively; and about errors in the surface figure of measurement object 150 according to the following equations.

$$\Phi_7 = 2k(x_7 + \zeta_7 + \xi_7) + 2kb\theta_P, \quad (10)$$

$$\Phi_8 = 2k(x_8 + \zeta_8 + \xi_8) - 2kb\theta_P \quad (11)$$

where $\zeta_7$ and $\zeta_8$ represent the stationary non-random effects of the gas and the other related effects of the gas along the $x_7$ and $x_8$ paths, respectively, of measurement beams 1126A and 1126B, respectively, and $\xi_7$ and $\xi_8$ represent the effects of surface figure errors of measurement object 150 at the location of spots 1136A and 1136B, respectively.

The difference in phases $\Phi_7 - \Phi_8$ is next computed to subsequently generate a quantity related to a FDP, $$\Phi_7 - \Phi_8 = 4kb\theta_P + 2k(\zeta_7 - \zeta_8) + 2k(\xi_7 - \xi_8). \quad (12)$$

The average of $\Phi_7 - \Phi_8$ is used to obtain information in situ about the effects of surface figure errors of measurement object 150 at the location of spots 136A and 136B, respectively. The phase difference $\Phi_7 - \Phi_8$ compensated for the measured effects of surface figure errors of measurement object 150 and compensated for changes in pitch using the results of measured values of $\Phi_1$ are inverted to obtain a value for the average value of $(\zeta_7 + \zeta_8)$. The average value of $(\zeta_7 + \zeta_8)$ is subsequently used to compensate for stationary non-random effects of the gas and the other related effects of the gas effects in the measured value of the displacement of measurement object 150 from the sum $(\Phi_7 + \Phi_8)$.

Measurement of pitch is obtained using Eq. (6). Measurements of the stationary non-random effects of the gas and the other related effects of the gas are obtained from the inversions of Eqs. (9) and (12) as subsequently described herein and compensation for the pitch contribution using the measured value of pitch. Measurement of the linear displacement is obtained from the average of the linear displacements $x_5$, $x_6$, $x_7$, and $x_8$ obtained from Eqs. (7), (8), (10), and (11) after compensation for the contributions of the stationary non-random effects of the gas and the other related effects of the gas using the measured values of the stationary non-random effects of the gas and the other related effects of the gas, compensation for the pitch term using the measured value of pitch and the beam spacing parameter b. Measurement of yaw is obtained from the difference of the average value of $x_5$ and $x_6$ and the average value of $x_7$ and $x_8$ compensated for the contributions of the stationary non-random effects of the gas and the other related effects of the gas using the measured values of the stationary non-random effects of the gas and the other related effects of the gas, and beam spacing parameter c (see FIG. 3*b*).

In general, values of a FDP can be measured by interferometer 100 either during the normal processing cycle of wafers and/or during periods other than a normal processing cycle of wafers, such as during an initialization or setup procedure.

In some embodiments, improved statistical accuracy in measured values of FDP can be obtained by taking advantage of the relatively low bandwidth of measured values of FDP compared to the bandwidth of the corresponding linear displacement measurements using averaging or low pass filtering.

In some embodiments, non-stationary non-random effects and the other related effects of the gas can be described mathematically by representing the non-stationary non-random effects as an ensemble of cells of gas and acoustic perturbations that move and propagate, respectively, through the measurement paths of beams 114A, 114B, 122A, 122B, 126A, 126B, 1126A, and 1126B in interferometer 100. The spatial distribution of cell or perturbation m of refractivity $[n(x,y,z,t)-1]_T$ is represented by a function $f_m(x,y,z,t)$ such that $$\zeta_i' = \int_{x_i'} [n(x_i', y, z, t) - 1]_T \, dx_i' \quad (13)$$

$$= \int_{x_i'} \left[ \sum_{m=1} f_m(x_i', y, z, t) \right] dx_i'.$$

Representation of the integration over the respective areas of beams 114A, 114B, 122A, 122B, 126A, 126B, 1126A, and 1126B in Eq. (13) is suppressed. Function $f_m(x_i', y, z, t)$ may vary from cell to cell or from perturbation to perturbation. A cell may represent the effect of a non-uniform composition of the gas or the effect of a turbulent eddy.

Inversion of Gas Stationary Non-Random Effects And Other Related Effects: Fourier Series Inversion Techniques The first difference parameter $FDP_{j,j+1}$, $j=5, 7$, given by Eq. (9) can be written in terms of stationary non-random effects of the gas and the other related effects of the gas, $\zeta'_i$, $i=5, 6, 7,$ and 8, as $$FDP_{j,j+1} = \zeta'_j(t) - \zeta'_{j+1}(t), \quad j=5,7. \quad (14)$$

The technique for inversion of stationary non-random effects of the gas and the other related effects of the gas is based on application of Fourier series techniques. Inversion of $FDP_{j,j+1}(t)$ may also be achieved by digital integration and Fourier transform techniques such as described in referenced U.S. Pat. No. 6,839,141 B2, Ser. No. 10/701,759, and Ser. No. 11/413,917 and U.S. Provisional Application No. 60/862,949. The Fourier series techniques are further described herein.

For a time period covering a time domain T $$\zeta'_{j,j+1}(t) = \sum_{m=1}^{N} A_m \cos\left[m2\pi \frac{(t-\bar{t})}{T}\right] + \sum_{m=1}^{N} B_m \sin\left[m2\pi \frac{(t-\bar{t})}{T}\right], \quad (15)$$

$$-\frac{1}{2} \leq \frac{(t-\bar{t})}{T} \leq \frac{1}{2}, \quad j=5, 7$$

where $\tau$ can in general will be a function of time, $\bar{t}$ is the average value of time t over the time domain (t−T) to t, and N is an integer determined by consideration of the temporal frequencies that are to be included in the series representation. A constant value is omitted from Eq. (15) since the average value of $\zeta'_i$ should statistically be zero. There will be a low frequency contribution to $\zeta'_i$ from environmental effects which can be measured for example by an array of wavelength monitors.

Using the definition of $FDP_{j,j+1}$ given by Eq. (14), the corresponding series for $FDP_{j,j+1}$ is next written as $$FDP_{j,j+1}(t) = 2\sum_{m=1}^{N} B_m \sin\left(m\pi \frac{\tau}{T}\right)\cos\left[m2\pi \frac{(t-\bar{t})}{T}\right] - \quad (16)$$

$$2\sum_{m=1}^{N} A_m \sin\left(m\pi \frac{\tau}{T}\right)\sin\left[m2\pi \frac{(t-\bar{t})}{T}\right],$$

$$-\frac{1}{2} \leq \frac{(t-\bar{t})}{T} \leq \frac{1}{2}, \quad j=5, 7.$$

A contracted form of Eq. (16) is obtained with the introduction of $A_m'$ and $B_m'$ as $$FDP_{j,j+1}(t) = \sum_{m=1}^{N} \left\{ \begin{array}{l} A_m' \cos\left[m2\pi \frac{(t-\bar{t})}{T}\right] + \\ B_m' \sin\left[m2\pi \frac{(t-\bar{t})}{T}\right] \end{array} \right\}, \quad (17)$$

$$-\frac{1}{2} \leq \frac{(t-\bar{t})}{T} \leq \frac{1}{2}, \quad j=5, 7$$

where $$A_m' = \int_{\frac{(t'-\bar{t})}{T}=-\frac{1}{2}}^{\frac{(t'-\bar{t})}{T}=\frac{1}{2}} \frac{2}{T} FDP_{j,j+1}(t')\cos\left[m2\pi \frac{(t'-\bar{t})}{T}\right] dt', \quad (18)$$

$$m > 0, \quad j = 5, 7;$$

$$B_m' = \int_{\frac{(t'-\bar{t})}{T}=-\frac{1}{2}}^{\frac{(t'-\bar{t})}{T}=\frac{1}{2}} \frac{2}{T} FDP_{j,j+1}(t')\sin\left[m2\pi \frac{(t'-\bar{t})}{T}\right] dt', \quad (19)$$

$$m > 0, \quad j = 5, 7.$$

With the expressions for $FDP_{j,j+1}(t)$ given by Eqs. (16) and (17), Eqs. (18) and (19) for $A_m'$ and $B_m'$, respectively, can be written in terms of $A_m$ and $B_m$ as $$A_p' = \int_{\frac{(t-\bar{t})}{T}=-\frac{1}{2}}^{\frac{(t-\bar{t})}{T}=\frac{1}{2}} \left\{ 2\cos\left[p2\pi \frac{(t-\bar{t})}{T}\right] \times \quad (20)\right.$$

$$\sum_{m=1}^{N} B_m \sin\left(m\pi \frac{\tau}{T}\right)\cos\left[m2\pi \frac{(t-\bar{t})}{T}\right] dt \Bigg\} -$$

$$\int_{\frac{(t-\bar{t})}{T}=-\frac{1}{2}}^{\frac{(t-\bar{t})}{T}=\frac{1}{2}} \left\{ 2\cos\left[p2\pi \frac{(t-\bar{t})}{T}\right] \times \right.$$

$$\sum_{m=1}^{N} A_m \sin\left(m\pi \frac{\tau}{T}\right)\sin\left[m2\pi \frac{(t-\bar{t})}{T}\right] dt \Bigg\}, \quad p > 0,$$

$$B_p' = \int_{\frac{(t-\bar{t})}{T}=-\frac{1}{2}}^{\frac{(t-\bar{t})}{T}=\frac{1}{2}} \left\{ 2\sin\left[p2\pi \frac{(t-\bar{t})}{T}\right] \times \quad (21)\right.$$

$$\sum_{m=1}^{N} B_m \sin\left(m\pi \frac{\tau}{T}\right)\cos\left[m2\pi \frac{(t-\bar{t})}{T}\right] dt \Bigg\} -$$

$$\int_{\frac{(t-\bar{t})}{T}=-\frac{1}{2}}^{\frac{(t-\bar{t})}{T}=\frac{1}{2}} 2\sin\left[p2\pi \frac{(t-\bar{t})}{T}\right] \times$$

$$\sum_{m=1}^{N} A_m \sin\left(m\pi \frac{\tau}{T}\right)\sin\left[m2\pi \frac{(t-\bar{t})}{T}\right] dt \Bigg\}, \quad p > 0.$$

Eqs. (20) and (21) can be written in the contracted matrix form $$\begin{pmatrix} A_1' \\ \vdots \\ A_N' \\ B_1' \\ \vdots \\ B_N' \end{pmatrix} = (M_{n,m}) \begin{pmatrix} A_1 \\ \vdots \\ A_N \\ B_1 \\ \vdots \\ B_N \end{pmatrix} \quad (22)$$

where the matrix elements $M_{n,m}$ of matrix $(M_{n,m})$ are given by corresponding factors in Eqs. (20) and (21).

For the situation where the deviation of $\tau$ from an average value $\bar{\tau}$ is a small fraction of $\bar{\tau}$, i.e., $|\tau-\bar{\tau}|/\bar{\tau} \ll 1$, the off diagonal matrix elements of matrix $(M_{n,m})$ are in general small compared to the corresponding diagonal matrix elements. In the case where the off diagonal matrix elements can be neglected, the matrix transformation expressed by Eq. (22) can be written in another contracted form where $A_p'$ and $B_p'$ are obtained from $A_p$ and $B_p$ by a complex rotation operator T. Complex rotation or transfer operator T has real and imaginary components $Re(T_p)$ and $Im(T_p)$ where $$A_p' = |T_p|[A_p\cos\vartheta + B_p\sin\vartheta], \quad (23)$$

$$B_p' = |T_p|[-A_p\sin\vartheta + B_p\cos\vartheta], \quad (24)$$

$$\tan\vartheta = \frac{Im(T_p)}{Re(T_p)}. \quad (25)$$

The real and imaginary components $Re(T_p)$ and $Im(T_p)$ are given by the formulae $$Re(T_p) = 0, \quad p > 0, \quad (26)$$

$$Im(T_p) = 2\sin\left(p\pi\frac{\tau}{T}\right), \quad p > 0. \quad (27)$$

The first zero in $|T_p|$ beyond the zero at p=0 occurs at p=250. For T=5 sec and $\tau$=20 msec for a beam spacing b=0.006 m and a speed of gas flow of 0.3 m/sec, the frequency $\omega/2\pi=p(1/T)$ is 50 Hz. at p=250 which is located in between typical values of frequency domains of the stationary non-random effects of the gas and the other related effects. The maximum value of the location of the first zero in $|T_p|$ beyond the zero at p=0 is determined by the maximum value of the vertical beam spacing for a given gas flow pattern.

Enhanced $FDP_{j,j+1}$ Sensitivity at Low Frequencies

The sensitivity of $FDP_{j,j+1}$ at low frequencies is increased in disclosed embodiments by a technique related to a discrete integration technique described in referenced U.S. patent application Ser. No. 10/701,759. The discrete integration technique takes advantage of the temporal properties of $\zeta_j(t)$ relative to $\zeta_{j+1}(t+\tau)$, j=5, 7, i.e., $\zeta_j(t) \cong \zeta_{j+1}(t+\tau)$, j=5, 7. This property is used in embodiments to increase the effective spacing between beams $x_j$ and $x_{j+1}$, j=5, 7, from b to qb where q=2, 3, .... The corresponding value for $FDP_{j,j+1}(t, q\tau)$ is given by the following formula $$FDP_{j,j+1}(t, qb) = \sum_{p=0}^{q} FDP_{j,j+1}(t+p\tau). \quad (28)$$

Figure 2B:
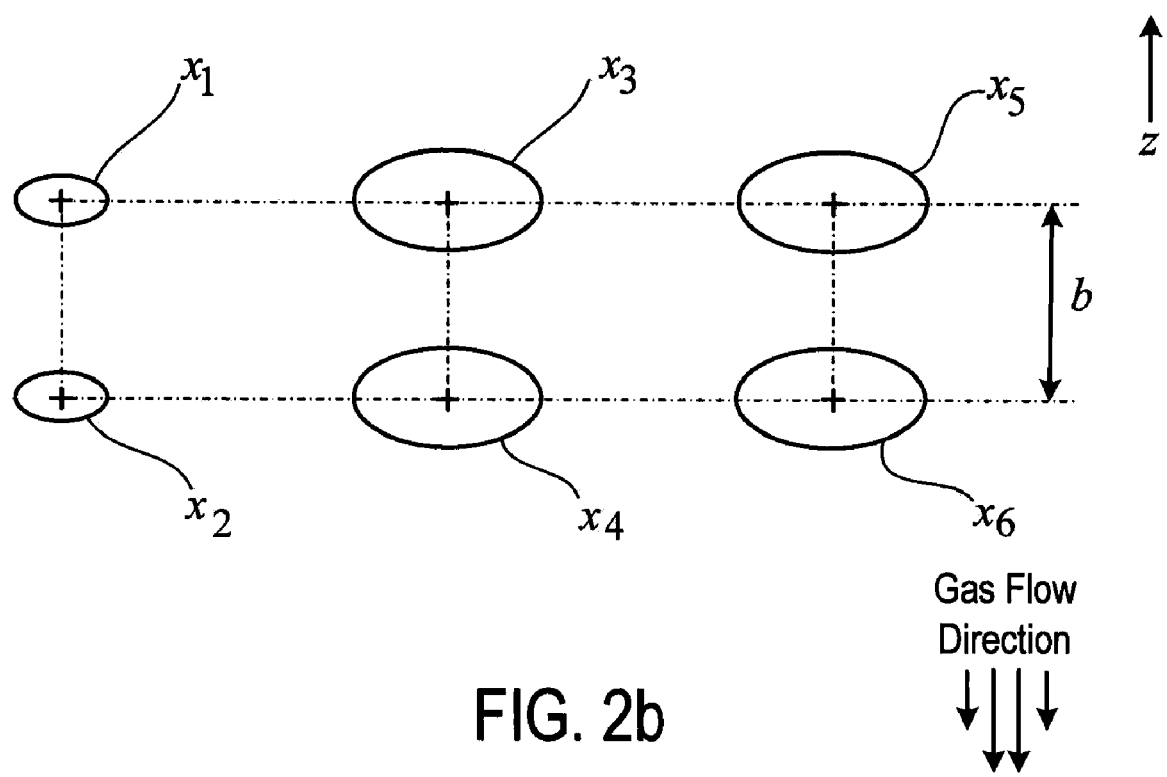

The first difference parameter $FDP_{j,j+1}(t, q\tau)$ is to a good approximation equal to the first difference parameter that would be obtained by interferometer 100 shown in FIGS. 2a and 2b where the spacing b has been replaced by the spacing qb.

Elimination of Effects of Gibbs Phenomenon

The effects of the Gibbs phenomenon associated with a discontinuity when using a Fourier series representation [see Section 14.5 entitled "Gibbs Phenomenon" in the book by G. Arfken *Mathematical Methods For Physicists*, Academic Press (1966)], may eliminated in disclosed embodiments by either of two related procedures. The two related procedures add a function $g_i(t)$, i=1, 2, to the measured values of $FDP_{j,j+1}$ to remove one or more discontinuities that may occur in the measured values of $FDP_{j,j+1}$ and temporal derivatives of $FDP_{j,j+1}$ at the limits of time domain $-\frac{1}{2} \leq (t-\bar{t})/T \leq \frac{1}{2}$. In the first related procedure, function $g_1(t)$ is selected such that $$\frac{d^p}{dt^p}[FDP_{j,j+1}(t) + g_1(t)]_{t/T=1/2} = \\ \frac{d^p}{dt^p}[FDP_{j,j+1}(t) + g_1(t)]_{t/T=-1/2}, \quad p \geq 0 \quad (29)$$

so as to remove one or more discontinuities that may occur in the measured values of $FDP_{j,j+1}$ and temporal derivatives of $FDP_{j,j+1}$ at the limits of time domain $-\frac{1}{2} \leq (t-\bar{t})/T \leq \frac{1}{2}$. A polynomial is chosen for the functional form of $g_1(t)$ in disclosed embodiments because the inversion of the respective $g_1(t)$ is easily obtained with effects of the Gibbs phenomenon compensated which is subsequently described herein. However, other functional forms may be selected for function $g_1(t)$ such as orthogonal functions, e.g., Chebyshev polynomials, without departing from the spirit and scope of disclosed embodiments.

To compensate for discontinuities up to the second temporal derivatives in $FDP_{j,j+1}$, a third order polynomial is used for function $g_1(t)$, i.e., $$g_1(t) = A + B\left(\frac{t-\bar{t}}{T}\right) + \frac{1}{2!}C\left(\frac{t-\bar{t}}{T}\right)^2 + \frac{1}{3!}D\left(\frac{t-\bar{t}}{T}\right)^3, \quad (30)$$

where A, B, C, and D are constants. The corresponding values for constants A, B, C, and D for which the conditions of Eq. (29) are satisfied are given by the formulae $$A = -FDP_{j,j+1}\left(\frac{1}{2}\right) - \left(\frac{1}{2}\right)B - \left(\frac{1}{4}\right)C - \left(\frac{1}{8}\right)D, \quad (31)$$

$$B = \begin{bmatrix} -FDP_{j,j+1}\left(\frac{1}{2}\right) + \\ FDP_{j,j+1}\left(-\frac{1}{2}\right) \end{bmatrix} - \frac{1}{4!}\begin{bmatrix} -FDP''_{j,j+1}\left(\frac{1}{2}\right) + \\ FDP''_{j,j+1}\left(-\frac{1}{2}\right) \end{bmatrix}, \quad (32)$$

$$C = \frac{1}{2}\left[-FDP'_{j,j+1}\left(\frac{1}{2}\right) + FDP'_{j,j+1}\left(-\frac{1}{2}\right)\right], \quad (33)$$

$$D = \frac{1}{3!}\left[-FDP''_{j,j+1}\left(\frac{1}{2}\right) + FDP''_{j,j+1}\left(-\frac{1}{2}\right)\right] \quad (34)$$

where $FDP_{j,j+1}'$ and $FDP_{j,j+1}''$ correspond to the first and second derivatives of $FDP_{j,j+1}$, respectively, with respect to $(t-\bar{t})/T$.

The inverted value $\zeta'_{j,j+1,I}$ for $\zeta'_{j,j+1}$ is obtained using the measured values of $A_m$ and $B_m$ in Eq. (15) as $$\zeta'_{j,j+1,I}(t) = \sum_{m=1}^{N} A_m\cos\left[m2\pi\frac{(t-\bar{t})}{T}\right] + \sum_{m=1}^{N} B_m\sin\left[m2\pi\frac{(t-\bar{t})}{T}\right] + \\ \langle FDP_{j,j+1}\rangle\left(\frac{T}{\tau}\right)\left[\frac{(t-\bar{t})}{T}\right] - \left\{\begin{array}{l} Inv(g_1) - \langle g_1\rangle\left(\frac{T}{\tau}\right) \\ \left[\frac{(t-\bar{t})}{T}\right] - \langle Inv(g_1)\rangle \end{array}\right\}, \quad (35)$$

$$-\frac{1}{2} \leq \frac{(t-\bar{t})}{T} \leq \frac{1}{2},$$

where $Inv(g_1)$ is obtained analytically from function $g_1$. Using the expression for function g given by Eq. (30), the corresponding function for $Inv(g_1)$ is given by the expression $$Invg_1(t) = A\left(\frac{t-\bar{t}}{T}\right) + B\left(\frac{t-\bar{t}}{T}\right)^2 + \frac{1}{2!}C\left(\frac{t-\bar{t}}{T}\right)^3 + \frac{1}{3!}D\left(\frac{t-\bar{t}}{T}\right)^4, \quad (36)$$

from represents the quantity obtained from the inversion of function $g_1$ and $\langle g_1 \rangle$ represents the average value of $g_1$ over the domain $|t-\bar{t}| \leq \frac{1}{2}$.

The function $Inv(g_1)$ either represents the result obtained using the Fourier series techniques described herein or the fit of a polynomial to the result obtained using the Fourier series techniques described herein wherein the order of the polynomial is one higher than the order of the polynomial used for function $g_1$.

Higher order polynomials may also be used for function $g_1(t)$. In addition, if only the effects of discontinuities in $FDP_{j,j+1}$ up to the first derivative need be eliminated, the value of constant D can be set equal to zero.

The second related procedure of the two related procedures forms an extended FDP, $FDP^E$, and applies the first related procedure to extended $FDP^E$. The extended $FDP^E$ is defined as $$FDP^E_{j,j+1}(t) \equiv \begin{cases} FDP_{j,j+1}[(t-\bar{t})/T], & -\frac{1}{2} \leq \frac{(t-\bar{t})}{T} \leq \frac{1}{2}, \\ -FDP_{j,j+1}[1-(t-\bar{t})/T], & \frac{1}{2} \leq \frac{(t-\bar{t})}{T} \leq \frac{3}{2} \end{cases} \quad (37)$$

where the second function $g_2(t)$ is selected to make $FDP_{j,j+1}{}^E(t)$ continuous at $(t-\bar{t})/T=\frac{1}{2}$ to remove one or more discontinuities that may occur in the measured values of extended $FDP_{j,j+1}{}^E(t)$ and temporal derivatives of extended $FDP_{j,j+1}{}^E(t)$ at the limits of time domain $-\frac{1}{2} \leq (t-\bar{t})/T \leq \frac{3}{2}$.

The corresponding series for extended $FDP_{j,j+1}{}^E(t)$ is written as $$FDP^E_{j,j+1}(t) = 2\sum_{m=1}^{N} B_m \sin\left(m\pi\frac{\tau}{T}\right)\cos\left[m2\pi\frac{(t-\bar{t})}{T}\right] - \quad (38)$$

$$2\sum_{m=1}^{N} A_m \sin\left(m\pi\frac{\tau}{T}\right)\sin\left[m2\pi\frac{(t-\bar{t})}{T}\right],$$

$$-\frac{1}{2} \leq \frac{(t-\bar{t})}{T} \leq \frac{3}{2}, j = 5, 7.$$

The remaining description of the second related procedure is the same as corresponding portions of the description given for the description of the first related procedure.

The advantage of the second related procedure is the all of the derivatives of extended $FDP_{j,j+1}{}^E(t)$ are continuous at $(t-\bar{t})/T=\frac{1}{2}$ by only requiring that extended $FDP_{j,j+1}{}^E(t)$ be continuous at $(t-\bar{t})/T=\frac{1}{2}$. This leads to a simpler functional form for $g_2(t)$ with improved results at the important end point $(t-\bar{t})/T=\frac{1}{2}$.

Systems Utilizing Reference Interferometers

Figure 4:
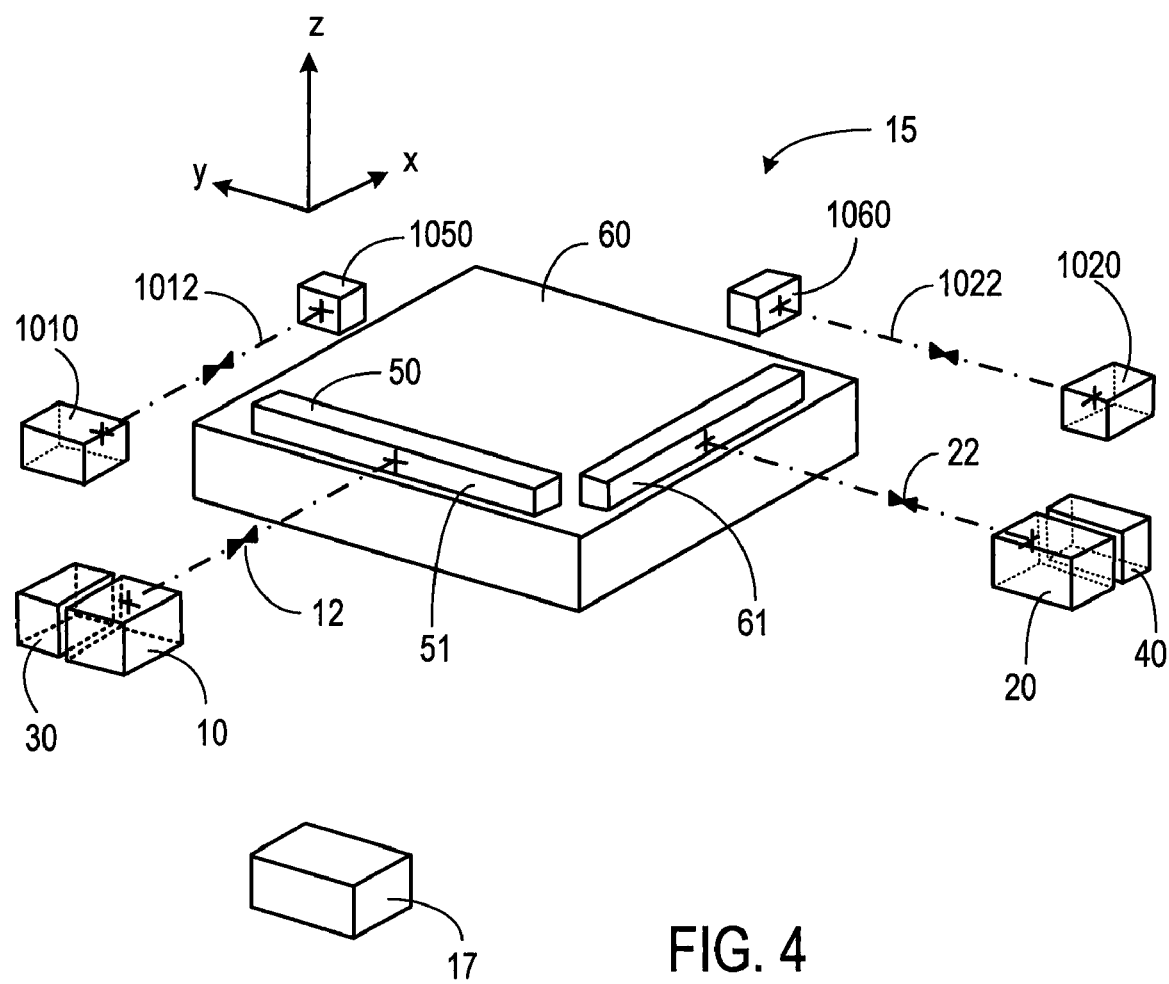
FIG. 4 is a schematic perspective view of another interferometer system that monitors the position of an object and compensates for effects of the optical properties of a gas in the measurement and/or reference paths of the interferometer system.

In some embodiments, interferometry systems can include one or more additional interferometers along with a multi-axis interferometer. For example, referring to FIG. 4, in some embodiments, interferometer system 15 includes interferometers 30 and 1010 mounted off-stage. Interferometer 30 is configured as a longitudinal reference interferometer (LRI) and interferometer 1010 is configured as a column reference interferometer (CRI). LRI 30 includes an interferometer, e.g., a high stability plane mirror interferometer (HSPMI), with fixed reference and measurement beam path lengths which are isolated from non-adiabatic changes in the optical properties of the gas. Other forms of a plane mirror configuration such as described in an article entitled "Differential interferometer arrangements for distance and angle measurements: Principles, advantages and applications" by C. Zanoni, *VDI Berichte* Nr. 749, pp 93-106 (1989) may be used for LRI 30 without departing from the scope and spirit of the present disclosure. The contents of the article by Zanoni are herein incorporated in their entirety by reference.

CRI 1010 is configured to monitor the position of a fixed measurement object 1050 with measurement beam 1012 and comprises an interferometer, e.g., a high stability plane mirror interferometer (HSPMI), with fixed reference and measurement path lengths. Measurement object 1050 is attached, for example, to the projection optic of the photolithographic apparatus. Other forms of a plane mirror configuration such as described by Zanoni (supra) may be used for CRI 1010. In embodiments, CRI 1010 is positioned sufficiently far from stage 16 so that the effects of turbulence due to stage movement in negligible in interferometer path 1012. In certain embodiments, CRI 1010 can be positioned relative to a gas inlet or exhaust so that gas from the inlet or to the exhaust flows through both interferometer path 1012 and path 12, introducing turbulence effects into measurements made using both interferometers 10 and 1010.

Also mounted off-stage are interferometers 40 and 1020. Interferometer 40 is configured as a LRI and interferometer 1020 is configured as a CRI. CRI 1020 is configured to monitor the position of a fixed measurement object 1060 with measurement beam 1022 and comprises an interferometer, e.g., a HSPMI, with fixed reference and measurement path lengths. Measurement object 1060 is attached for example to the projection optic of the photolithographic apparatus. Other forms of a plane mirror configuration such as described by Zanoni (supra) may be used for CRI 1020 without departing from the scope and spirit of the present disclosure.

In some embodiments, LRIs 30 and 40 are wavelength monitors such as described in commonly owned U.S. Pat. No. 4,685,803 and No. 4,733,967. Both of the patents are by G. E. Sommargren and the contents thereof are herein incorporated in their entirety by reference.

Two or more of interferometers 10, 20, 30, 40, 1010, and 1020 can use the same light source for their respective input beams. In some embodiments, a single light source is used to provide input beams to all interferometers.

Other configurations of interferometry systems are also possible. For example, while the system shown in FIG. 4 includes only two LRI's, systems can include more or fewer LRI's. For example, systems can include an array of several (i.e., more than two) LRI's, each configured to provide information about adiabatic changes in the optical properties of the gas in the system for a variety of different positions in the lithography tool, providing additional information regarding the isotropy (or lack thereof) of the adiabatic changes.

In some embodiments, interferometer subsystems 10 and 20 can include apparatus and methods of dispersive interferometry in combination with apparatus and methods of non-dispersive techniques for the compensation of effects of a dispersive medium such as a gas in the measurement and/or reference beam paths of the respective interferometer subsystems 10 and 20. Interferometer subsystems 10 and 20 may include dispersion interferometers such as a two wavelength source and a monitor for measurement of an intrinsic property of a gas such as the reciprocal dispersive power in interferometry subsystem 15.

Initialization of LRI, CRI, and Interferometer System 100

In single stage lithography tools, interferometers 10, 20, 30, 40, 1010, and 1020 of interferometer system 15 do not necessarily need to be initialized at the exchange of each wafer being processed because only the same stage is used for each exposure and the interferometers are monitoring the same stage mirror at each step of the exposure and wafer exchange processes. Thus, processing of information from interferometers 10, 20, 30, 40, 1010, and 1020 for compensation for stationary non-random effects of a gas and the other related effects of the gas can be simpler in single stage lithography tools than in multi-stage tools. In contrast, in a dual stage lithography tool where stages are exchanged, interferometers 10, 20, 30, and 40 may need to be initialized at each exchange of stages if there is not a "hand off" between certain interferometers. However, interferometers 1010 and 1020 will not need to be initialized at each exchange of a stage or wafer chuck. The effect of the subsequent initializations of interferometers 10, 20, 30, and 40 on the inversion of stationary non-random effects of a gas and other related effects of the gas should be taken into account wherein the impact of the subsequent initializations to reduce the accuracy of the inversions immediately after the initializations.

In acquisition of alignment mark measurements following immediately after the initializations, one way to compensate for the reduction of accuracy of the corresponding inversions is to increase the time duration of the alignment mark measurements to improve statistical accuracy. Another way to reduce the effect of the reduction of accuracy of the inversions immediately after the initializations is to reduce the speed of the stage motion which reduces the amount of stationary non-random effects of a gas and other related effects of the gas generated during the period between the initialization and, for example, the first exposure of the wafer.

Compensation for Effects of Vibrations

The different properties of LRI, CRI, and interferometer system 100 can be identified by spectral analyses of respective electric interference signals and compensated by frequency filtering the signal data, e.g., before use in the data processing algorithms for information about the position of stage 16 compensated for effects of stationary non-random effects of a gas and the other related effects of the gas. Vibrations, for example, generally manifest at relatively high frequencies (e.g., about 100 Hz or more), and can be isolated using a band pass filter.

Use of Interferometry Metrology Systems with Encoder Metrology Systems

In some embodiments, interferometer systems can be used in conjunction with encoder systems to provide accurate measurements of a stage position in a lithography tool. For example, stationary non-random effects of a gas can be measured as the change between the relative position measurements obtained with an interferometer metrology system and obtained with a planar encoder metrology system that occurs between a relatively slow scan or step and stare scan mode and the scanning mode used in the processing of a wafer.

The advantage of a relative measurement procedure such as used in disclosed embodiments is the elimination or the significant reduction of non-linear non-cyclic effects such as geometric errors, effects of surface figure errors of stage mirrors, effects of beam shear in interferometers generated by changes in orientation of measurement objects, and stationary effects such as generated by body deformation of a lithography tool due to stage motion excluding the effects of deformation of stage mirrors due to stage motion.

A further advantage of a relative measurement procedure is that effects of deformation of stage mirrors due to stage motion are included in the measured values of stationary non-random effects. For the disclosed embodiments, it is not necessary to identify the relative contributions of stationary non-random effects of a gas and of stationary non-random effects due to deformation of stage mirrors in the measured values of stationary non-random effects.

Figure 5:
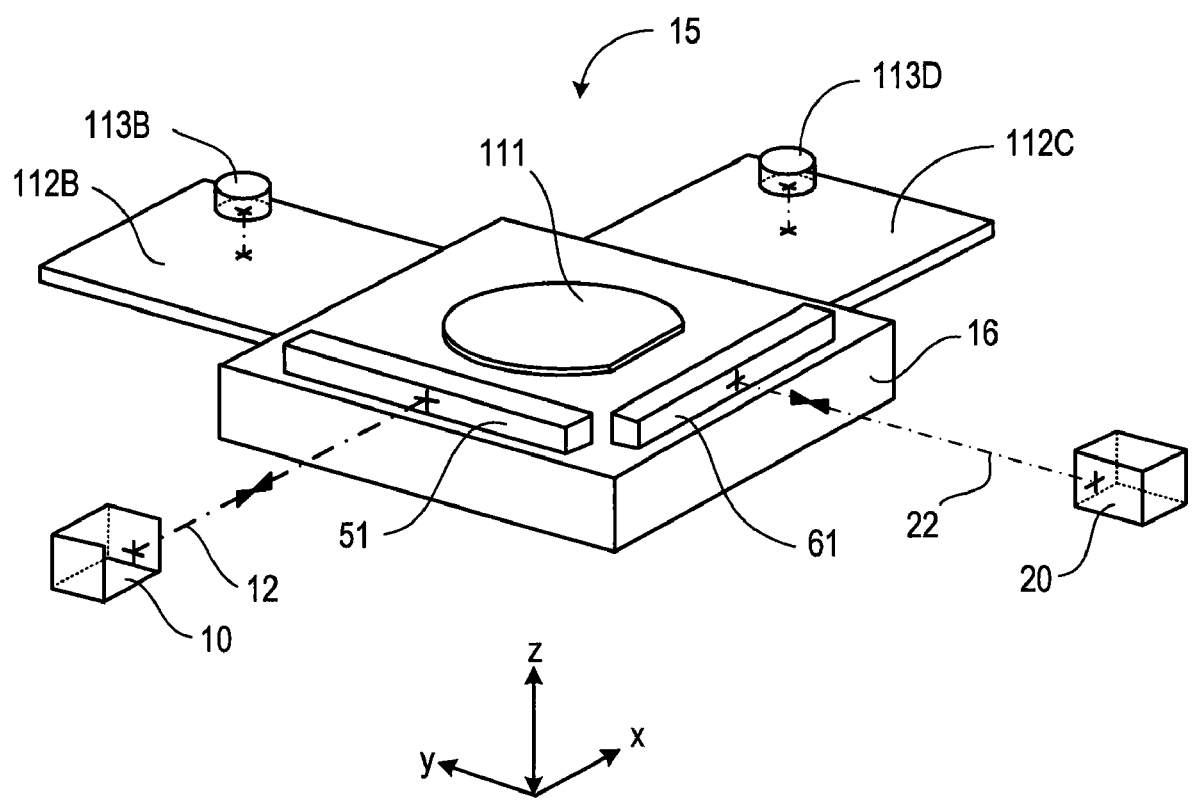
FIG. 5 is a schematic perspective view of an interferometer system and encoders system that monitors the position of an object and compensates for effects of the optical properties of a gas in the measurement and/or reference paths of the interferometer system.

The planar encoder metrology system generates information about linear and angular displacements of a measurement object with a reduced sensitivity to stationary non-random effects of the gas and stationary non-random deformation of the measurement object which however affect the corresponding information obtained by the interferometer metrology system of the measurement object. Referring to FIG. 5, for example, in some embodiments, planar encoder scales 112B and 112C are attached to stage 16 and the position of the planar encoder scale is measured using corresponding encoder heads 113B and 113C, respectively. Planar encoder scale 112B and head 113B are configured to monitor the location of stage 16 along the y-axis, parallel to interferometer axis 22, while planar encoder scale 112C and 113C are configured to monitor the location of stage 16 along the x-axis, parallel to interferometer axis 12. Encoder heads 113B and 113C can be in communication with electronic processor 17.

A planar or linear encoder herein referred to as a planar encoder may be configured such that the effects of gas in the respective measurement paths do not affect the repeatability of position measurements of the planar encoder at the nanometer and sub-nanometer level.

The processing of information in a stage metrology system including an interferometer metrology system and encoder metrology system generates superheterodyne signal quadratures and respective superheterodyne phases such as described in U.S. Provisional Patent Application No. 60/862,949 and U.S. patent application Ser. No. 11/941,012, filed Nov. 15, 2007, where the superheterodyne phases includes effects of errors of the planar encoder system. The entire contents of applications 60/862,949 and Ser. No. 11/941,012 are incorporated herein by reference. The sensitivity of the contribution of stationary non-random effects by the encoder metrology system to the superheterodyne phases is negligible or a significantly reduced. The classification of the negligible or significantly reduced sensitivity of the contribution to the superheterodyne phases by the encoder metrology system is based on a comparison to the sensitivity of corresponding heterodyne or homodyne phases of the interferometer system to stationary non-random effects.

The phases of the superheterodyne signal quadratures include primarily only low frequency components such as generated by stationary non-random effects, other related effects of a gas, atmospheric turbulence in measurement and reference paths of the interferometer system and errors of the interferometer and encoder metrology systems such as cyclic errors, non-linear non-cyclic errors, geometric errors, Abbé offset errors, and effects of changes in temperature of the lithography tool. The phases of the superheterodyne signal quadratures can be subsequently processed to measure in situ the changes that are generated by changing for example from a step and stare mode to a scanning mode. The stationary non-random effects are obtained as the average of the measured phases of the superheterodyne signal quadratures for the different scan modes to reduce the contributions of random effects and statistical errors such as arise in electronic processing.

Measurement of Stationary Effects not Related to Gas Effects

Effects of stationary non-random effects not related to the gas, e.g., body deformations from stage motion and changes in the temperature of the lithography tool, can introduce errors in, e.g., measurements made by a CRI. Changes in the temperature of the lithography tool will generally contribute to errors in measurements made by a CRI at frequencies below or of the order of 0.01 Hz. However, stationary non-random effects that result from body deformation generated by stage motion can lie in the frequency range of stationary non-random effects of the gas and other related effects of the gas.

Because of the location of a CRI, the stationary non-random effects of the gas in the lithography tool will, in general, be reduced compared to the magnitude of the contribution of the stationary non-random effects of the gas to interferometer metrology systems such as interferometer system 100 shown in FIGS. 2a and 2b. As a result, the contribution of stationary non-random effects not related to the gas, e.g., body deformation from stage motion, to errors in measurements made by a CRI can be measured by a procedure analogous to the procedure used to measure the stationary non-random effects of the gas to interferometer metrology systems such as interferometer system 100. A corresponding superheterodyne phase can be generated from the signals from the encoder metrology system and from the respective CRI. The stationary non-random effects not related to the gas can be obtained as the average of the measured phases of the respective superheterodyne signal quadratures for the different scan modes to reduce the contributions of random effects and statistical errors such as arise in electronic processing.

The contribution of stationary non-random effects not related to the gas, e.g., body deformation from stage motion, to errors in measurements made by a CRI can be measured in certain embodiments from information obtained during a general alignment procedure for the lithography tool.

In embodiments, the measured contribution of stationary non-random effects not related to the gas to information obtained with a CRI can be subtracted from the information subsequently used in the compensation for stationary non-random effects of the gas and other related effects of the gas.

Cyclic Errors

In addition to compensating for variations in the optical properties of a gas, phase measurements can be compensated for still other sources of errors. For example, cyclic errors that are present in the linear displacement measurements are eliminated and/or compensated by use of one of more techniques such as described in commonly owned U.S. patent application Ser. No. 10/097,365 entitled "CYCLIC ERROR REDUCTION IN AVERAGE INTERFEROMETRIC MEASUREMENTS" and Ser. No. 10/616,504 entitled "CYCLIC ERROR COMPENSATION IN INTERFEROMETRY SYSTEMS," which claims priority to U.S. Provisional Application No. 60/394,418 entitled "ELECTRONIC CYCLIC ERROR COMPENSATION FOR LOW SLEW RATES." Each of the utility applications and the provisional patent application are all by Henry A. Hill and the contents of each thereof are incorporated herein in their entireties by reference.

An example of another cyclic error compensation technique is described in commonly owned U.S. patent application Ser. No. 10/287,898 entitled "INTERFEROMETRIC CYCLIC ERROR COMPENSATION" which claims priority to U.S. Provisional Application No. 60/337,478 entitled "CYCLIC ERROR COMPENSATION AND RESOLUTION ENHANCEMENT." The utility application and the provisional patent application are each by Henry A. Hill and the contents thereof are incorporated herein in their entireties by reference.

Another example of a cyclic error compensation technique is described in U.S. patent application Ser. No. 10/174,149 entitled "INTERFEROMETRY SYSTEM AND METHOD EMPLOYING AN ANGULAR DIFFERENCE IN PROPAGATION BETWEEN ORTHOGONALLY POLARIZED INPUT BEAM COMPONENTS" which claims priority to U.S. Provisional Patent Application 60/303,299 entitled "INTERFEROMETRY SYSTEM AND METHOD EMPLOYING AN ANGULAR DIFFERENCE IN PROPAGATION BETWEEN ORTHOGONALLY POLARIZED INPUT BEAM COMPONENTS." The utility application and the provisional patent application are each by Henry A. Hill and Peter de Groot and the contents both thereof are incorporated herein in their entirety by reference.

A further example of a cyclic error compensation technique is described in commonly owned U.S. Provisional Patent Application No. 60/314,490 and corresponding utility application Ser. No. 10/218,968 entitled "TILTED INTERFEROMETER" by Henry A. Hill. The contents of the provisional patent application and the utility application are incorporated herein in their entireties by reference.

Other techniques for cyclic error compensation include those described in U.S. Pat. No. 6,137,574 entitled "SYSTEMS AND METHODS FOR CHARACTERIZING AND CORRECTING CYCLIC ERRORS IN DISTANCE MEASURING AND DISPERSION INTERFEROMETRY;" No. 6,252,668 B1 entitled "SYSTEMS AND METHODS FOR QUANTIFYING NON-LINEARITIES IN INTERFEROMETRY SYSTEMS;" and No. 6,246,481 entitled "Systems And Methods For Quantifying Nonlinearities In Interferometry Systems." All three of the cited patents are by Henry A. Hill and the contents thereof of the three cited patents are herein incorporated in their entirety by reference.

Steps in Data Processing Algorithm

Figure 6:
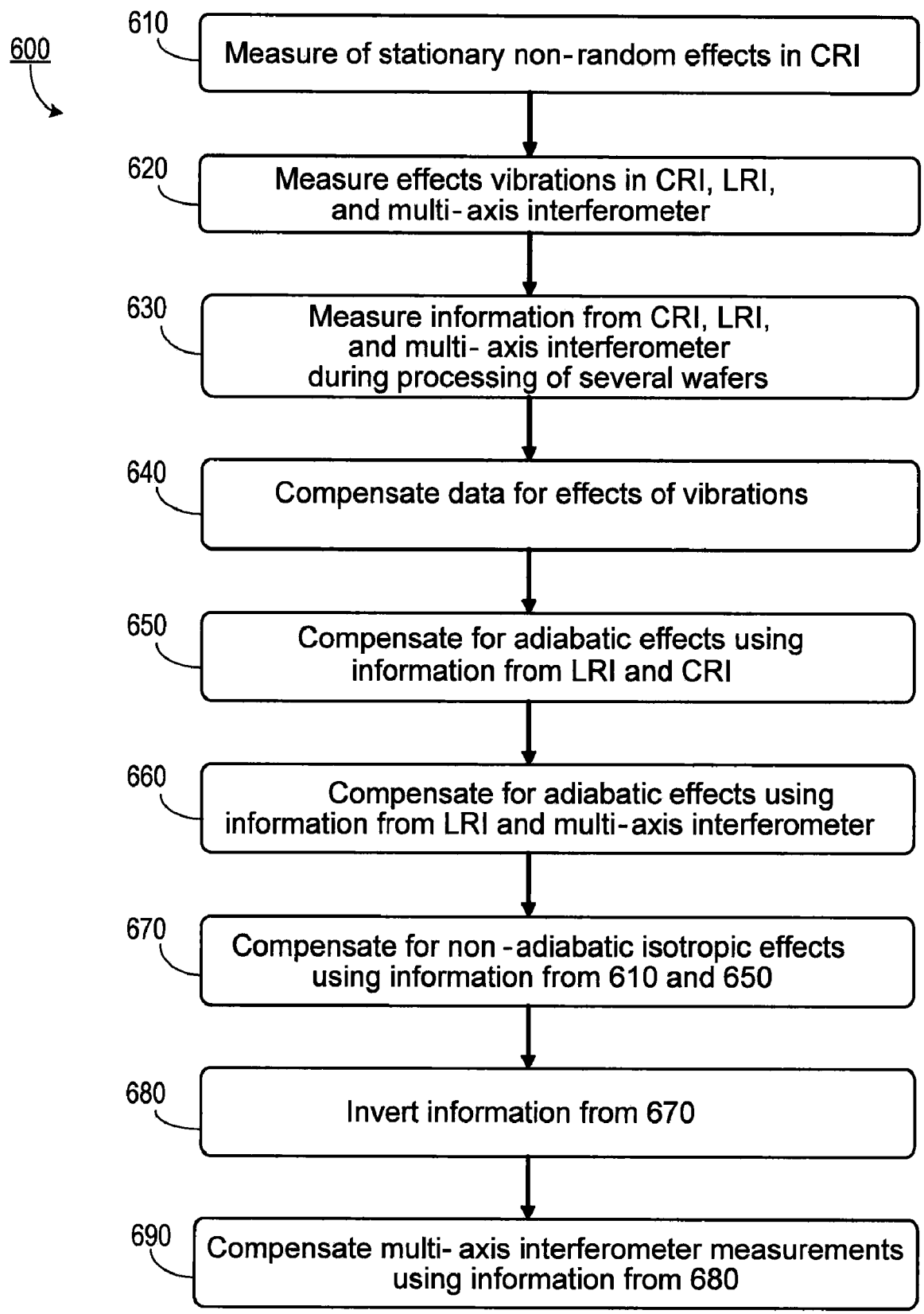
FIG. 6 is a flowchart showing steps in example of an algorithm for implementing error correction for interferometric stage mirror measurements
Figure 7:
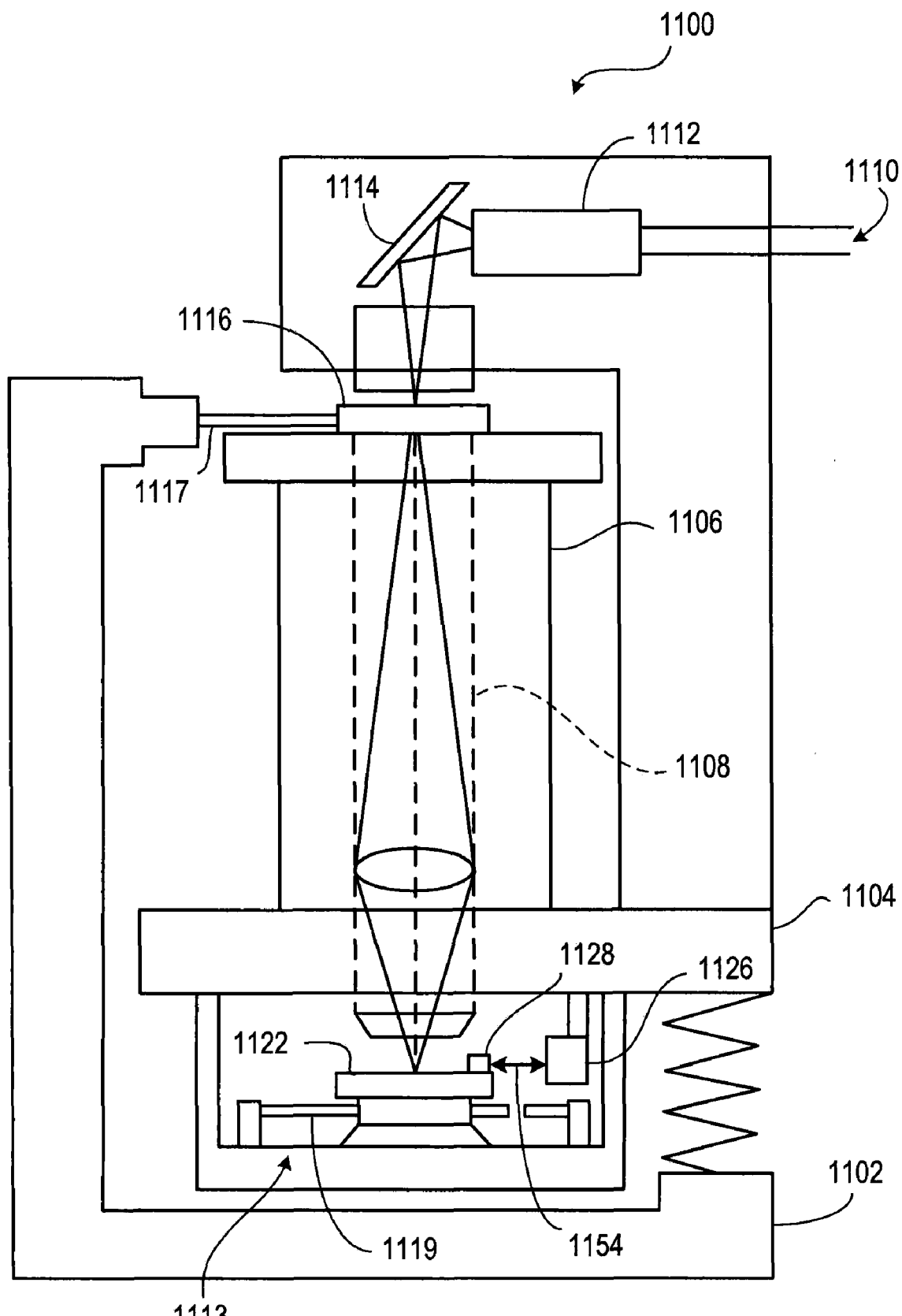
FIG. 7 is a schematic diagram of a lithography tool.

While the error compensation techniques discussed above can be implemented in a variety of different ways, FIG. 6 shows an example of an algorithm 600 for implementing error correction for interferometric stage mirror measurements. Step one (610) in the data processing algorithm is the measurement of stationary non-random effects in CRI not associated with stationary non-random effects of the gas and the other related effects of the gas.

Step two (620) in the data processing algorithm is the measurement of the effects of vibrations in LRI, CRI, and interferometer system 100.

Step three (630) in the data processing algorithm is the measurement of information from LRI, CRI, and interferometer system 100 obtained during the processing of a series of wafers by a lithography tool.

Step four (640) in the data processing algorithm is the compensation for the different effects of vibrations to information from LRI, CRI, and interferometer system 100. Step four compensates for effects of vibrations.

Step five (650) in the data processing algorithm is the subtraction of information obtained by the vibration compensated LRI from the information obtained from vibration compensated CRI scaled according to the respective relative measurement beam path lengths. Step five compensates for adiabatic effects.

Step six (660) in the data processing algorithm is the subtraction of information obtained by the vibration compensated LRI from the information obtained from vibration compensated interferometer system 100 scaled according to the respective relative measurement beam path lengths. Step six compensates for adiabatic effects.

Step seven (670) in the data processing algorithm is the subtraction of information obtained from vibration compensated CRI (from step five) and information about the stationary non-random effects not related to the gas (from step one) from information obtained from vibration compensated information from interferometer system 100 (from step six) scaled according to the respective relative measurement beam path lengths. Step seven corresponds to compensation for non-adiabatic isotropic effects of the gas and other related effects of the gas and compensation for stationary non-random effects not related to the gas. The subtractions take into account the effects of the time delay for non-adiabatic isotropic effects to be transported from CRI to interferometer system 100 and the frequency domain of the non-adiabatic isotropic effects of the gas and other related effects of the gas.

Step eight (680) in the data processing algorithm is the inversion of the information from interferometer system 100 obtained in step seven for measured values of the stationary non-random effects of the gas and the other related effects of the gas. Step eight corresponds to determination of non-adiabatic non-isotropic effects of the gas and other related effects of the gas in the measurement beam paths of interferometer system 100.

Step nine (690) in the data processing algorithm is the subtraction of the inverted information about stationary non-random effects of the gas and the other related effects of the gas (obtained in step eight) from the information obtained in interferometer system 100 about the position including the angular orientation of stage 16. Step nine corresponds to compensation for non-adiabatic non-isotropic effects of the gas and other related effects of the gas. The subtractions take into account the frequency domain of the non-adiabatic non-isotropic effects of the gas and other related effects of the gas.

In general, any of the analysis methods described above can be implemented in computer hardware or software, or a combination of both. For example, in some embodiments, electronic processor 17 can be part of a module that can be installed in a computer and connected to one or more interferometers and/or encoders and configured to perform analysis of signals from the interferometers and/or encoders. Analysis can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis methods can also be implemented as a computer-readable storage medium, configured with a computer program, where the storage medium so configured causes a computer to operate in a specific and predefined manner to perform the functions described herein.

Lithography Tool Applications

As discussed previously, lithography tools are especially useful in lithography applications used in fabricating large scale integrated circuits such as computer chips and the like. Lithography is the key technology driver for the semiconductor manufacturing industry. Overlay improvement is one of the five most difficult challenges down to and below 100 nm line widths (design rules), see, for example, the *Semiconductor Industry Roadmap*, p. 82 (1997).

Overlay depends directly on the performance, i.e., accuracy and precision, of the distance measuring interferometers used to position the wafer and reticle (or mask) stages. Since a lithography tool may produce $50-100 M/year of product, the economic value from improved performance distance measuring interferometers is substantial. Each 1% increase in yield of the lithography tool results in approximately $1 M/year economic benefit to the integrated circuit manufacturer and substantial competitive advantage to the lithography tool vendor.

The function of a lithography tool is to direct spatially patterned radiation onto a photoresist-coated wafer. The process involves determining which location of the wafer is to receive the radiation (alignment) and applying the radiation to the photoresist at that location (exposure).

To properly position the wafer, the wafer includes alignment marks on the wafer that can be measured by dedicated sensors. The measured positions of the alignment marks define the location of the wafer within the tool. This information, along with a specification of the desired patterning of the wafer surface, guides the alignment of the wafer relative to the spatially patterned radiation. Based on such information, a translatable stage supporting the photoresist-coated wafer moves the wafer such that the radiation will expose the correct location of the wafer.

During exposure, a radiation source illuminates a patterned reticle, which scatters the radiation to produce the spatially patterned radiation. The reticle is also referred to as a mask, and these terms are used interchangeably below. In the case of reduction lithography, a reduction lens collects the scattered radiation and forms a reduced image of the reticle pattern. Alternatively, in the case of proximity printing, the scattered radiation propagates a small distance (typically on the order of microns) before contacting the wafer to produce a 1:1 image of the reticle pattern. The radiation initiates photochemical processes in the resist that convert the radiation pattern into a latent image within the resist.

Interferometry metrology systems, such as those discussed previously, are important components of the positioning mechanisms that control the position of the wafer and reticle, and register the reticle image on the wafer. If such interferometry systems include the features described above, the accuracy of distances measured by the systems can be increased and/or maintained over longer periods without offline maintenance, resulting in higher throughput due to increased yields and less tool downtime.

In general, the lithography system, also referred to as an exposure system, typically includes an illumination system and a wafer positioning system. The illumination system includes a radiation source for providing radiation such as ultraviolet, visible, x-ray, electron, or ion radiation, and a reticle or mask for imparting the pattern to the radiation, thereby generating the spatially patterned radiation. In addition, for the case of reduction lithography, the illumination system can include a lens assembly for imaging the spatially patterned radiation onto the wafer. The imaged radiation exposes resist coated onto the wafer. The illumination system also includes a mask stage for supporting the mask and a positioning system for adjusting the position of the mask stage relative to the radiation directed through the mask. The wafer positioning system includes a wafer stage for supporting the wafer and a positioning system for adjusting the position of the wafer stage relative to the imaged radiation. Fabrication of integrated circuits can include multiple exposing steps. For a general reference on lithography, see, for example, J. R. Sheats and B. W. Smith, in *Microlithography: Science and Technology* (Marcel Dekker, Inc., New York, 1998), the contents of which is incorporated herein by reference.

Interferometry systems described above can be used to precisely measure the positions of each of the wafer stage and mask stage relative to other components of the exposure system, such as the lens assembly, radiation source, or support structure. In such cases, the interferometry system can be attached to a stationary structure and the measurement object attached to a movable element such as one of the mask and wafer stages. Alternatively, the situation can be reversed, with the interferometry system attached to a movable object and the measurement object attached to a stationary object.

More generally, such interferometry systems can be used to measure the position of any one component of the exposure system relative to any other component of the exposure system, in which the interferometry system is attached to, or supported by, one of the components and the measurement object is attached, or is supported by the other of the components.

An example of a lithography tool 1100 using an interferometry system 1126 is shown in FIG. 5. The interferometry system is used to precisely measure the position of a wafer (not shown) within an exposure system. Here, stage 1122 is used to position and support the wafer relative to an exposure station. Scanner 1100 includes a frame 1102, which carries other support structures and various components carried on those structures. An exposure base 1104 has mounted on top of it a lens housing 1106 atop of which is mounted a reticle or mask stage 1116, which is used to support a reticle or mask. A positioning system for positioning the mask relative to the exposure station is indicated schematically by element 1117. Positioning system 1117 can include, e.g., piezoelectric transducer elements and corresponding control electronics. Although, it is not included in this described embodiment, one or more of the interferometry systems described above can also be used to precisely measure the position of the mask stage as well as other moveable elements whose position must be accurately monitored in processes for fabricating lithographic structures (see supra Sheats and Smith *Microlithography: Science and Technology*).

Suspended below exposure base 1104 is a support base 1113 that carries wafer stage 1122. Stage 1122 includes a plane mirror 1128 for reflecting a measurement beam 1154 directed to the stage by interferometry system 1126. A positioning system for positioning stage 1122 relative to interferometry system 1126 is indicated schematically by element 1119. Positioning system 1119 can include, e.g., piezoelectric transducer elements and corresponding control electronics. The measurement beam reflects back to the interferometry system, which is mounted on exposure base 1104. The interferometry system can be any of the embodiments described previously.

During operation, a radiation beam 1110, e.g., an ultraviolet (UV) beam from a UV laser (not shown), passes through a beam shaping optics assembly 1112 and travels downward after reflecting from mirror 1114. Thereafter, the radiation beam passes through a mask (not shown) carried by mask stage 1116. The mask (not shown) is imaged onto a wafer (not shown) on wafer stage 1122 via a lens assembly 1108 carried in a lens housing 1106. Base 1104 and the various components supported by it are isolated from environmental vibrations by a damping system depicted by spring 1120.

In other embodiments of the lithographic scanner, one or more of the interferometry systems described previously can be used to measure distance along multiple axes and angles associated for example with, but not limited to, the wafer and reticle (or mask) stages. Also, rather than a UV laser beam, other beams can be used to expose the wafer including, e.g., x-ray beams, electron beams, ion beams, and visible optical beams.

Figure 8A:
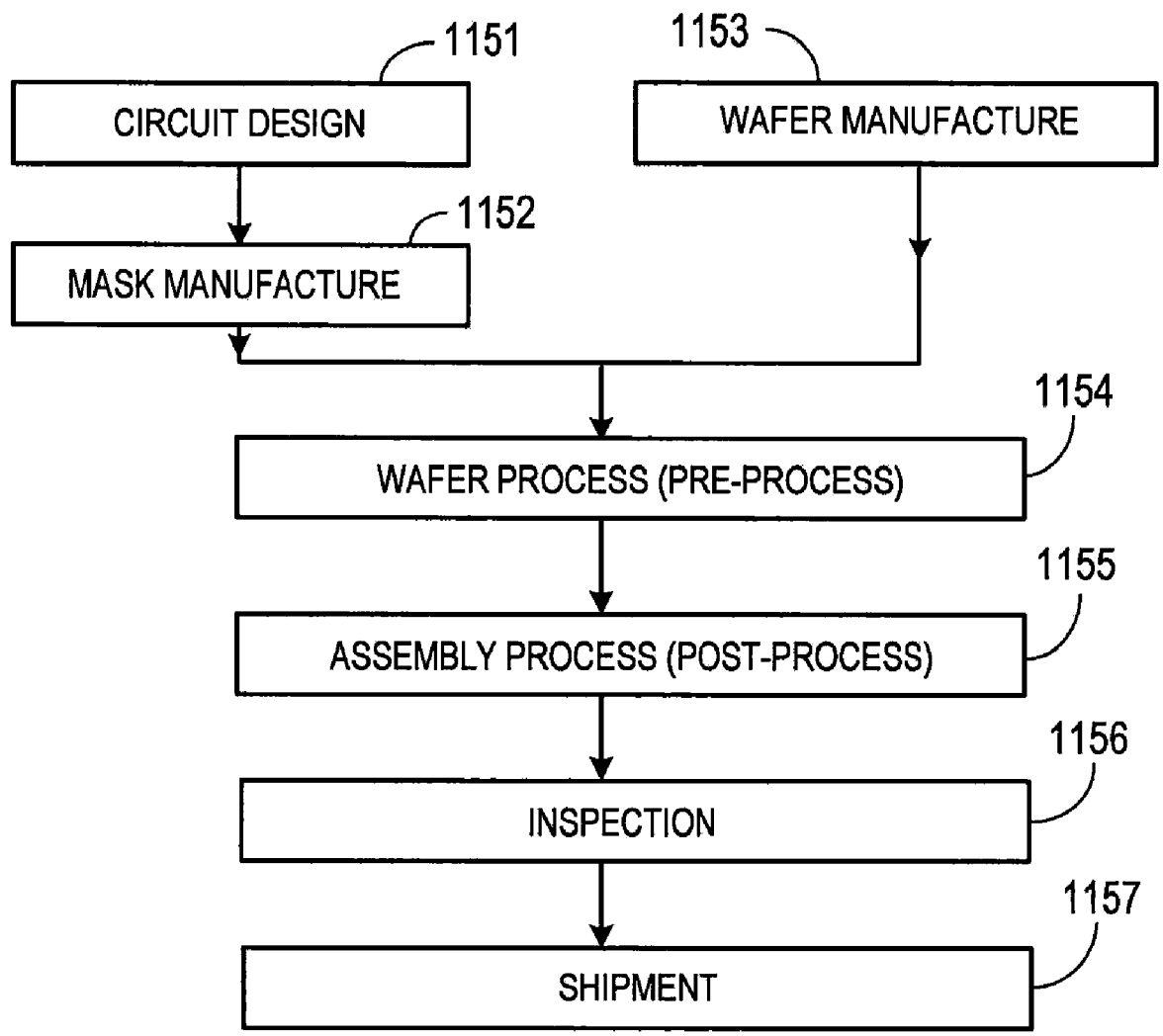
FIG. 8a and FIG. 8b are flow charts that describe steps for making integrated circuits.

In some embodiments, the lithographic scanner can include what is known in the art as a column reference. In such embodiments, the interferometry system 1126 directs the reference beam (not shown) along an external reference path that contacts a reference mirror (not shown) mounted on some structure that directs the radiation beam, e.g., lens housing 1106. The reference mirror reflects the reference beam back to the interferometry system. The interference signal produce by interferometry system 1126 when combining measurement beam 1154 reflected from stage 1122 and the reference beam reflected from a reference mirror mounted on the lens housing 1106 indicates changes in the position of the stage relative to the radiation beam. Furthermore, in other embodiments the interferometry system 1126 can be positioned to measure changes in the position of reticle (or mask) stage 1116 or other movable components of the scanner system. Finally, the interferometry systems can be used in a similar fashion with lithography systems involving steppers, in addition to, or rather than, scanners. As is well known in the art, lithography is a critical part of manufacturing methods for making semiconducting devices. For example, U.S. Pat. No. 5,483,343 outlines steps for such manufacturing methods. These steps are described below with reference to FIGS. 8*a* and 8*b*. FIG. 8*a* is a flow chart of the sequence of manufacturing a semiconductor device such as a semiconductor chip (e.g., IC or LSI), a liquid crystal panel or a CCD. Step 1151 is a design process for designing the circuit of a semiconductor device. Step 1152 is a process for manufacturing a mask on the basis of the circuit pattern design. Step 1153 is a process for manufacturing a wafer by using a material such as silicon.

Step 1154 is a wafer process which is called a pre-process wherein, by using the so prepared mask and wafer, circuits are formed on the wafer through lithography. To form circuits on the wafer that correspond with sufficient spatial resolution those patterns on the mask, interferometric positioning of the lithography tool relative the wafer is necessary. The interferometry methods and systems described herein can be especially useful to improve the effectiveness of the lithography used in the wafer process.

Step 1155 is an assembling step, which is called a post-process wherein the wafer processed by step 1154 is formed into semiconductor chips. This step includes assembling (dicing and bonding) and packaging (chip sealing). Step 1156 is an inspection step wherein operability check, durability check and so on of the semiconductor devices produced by step 1155 are carried out. With these processes, semiconductor devices are finished and they are shipped (step 1157).

Figure 8B:
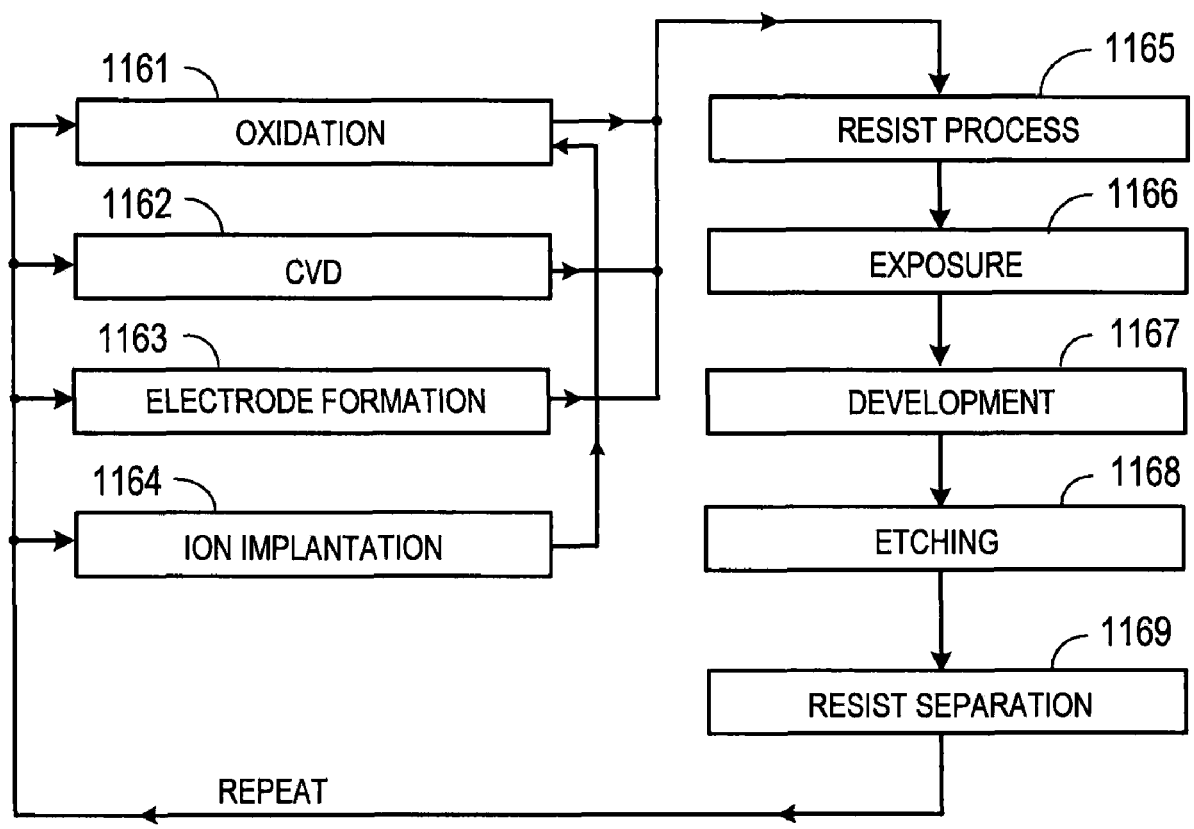

FIG. 8*b* is a flow chart showing details of the wafer process. Step 1161 is an oxidation process for oxidizing the surface of a wafer. Step 1162 is a CVD process for forming an insulating film on the wafer surface. Step 1163 is an electrode forming process for forming electrodes on the wafer by vapor deposition. Step 1164 is an ion implanting process for implanting ions to the wafer. Step 1165 is a resist process for applying a resist (photosensitive material) to the wafer. Step 1166 is an exposure process for printing, by exposure (i.e., lithography), the circuit pattern of the mask on the wafer through the exposure apparatus described above. Once again, as described above, the use of the interferometry systems and methods described herein improve the accuracy and resolution of such lithography steps.

Step 1167 is a developing process for developing the exposed wafer. Step 1168 is an etching process for removing portions other than the developed resist image. Step 1169 is a resist separation process for separating the resist material remaining on the wafer after being subjected to the etching process. By repeating these processes, circuit patterns are formed and superimposed on the wafer.

The interferometry systems described above can also be used in other applications in which the relative position of an object needs to be measured precisely. For example, in applications in which a write beam such as a laser, x-ray, ion, or electron beam, marks a pattern onto a substrate as either the substrate or beam moves, the interferometry systems can be used to measure the relative movement between the substrate and write beam.

Figure 9:
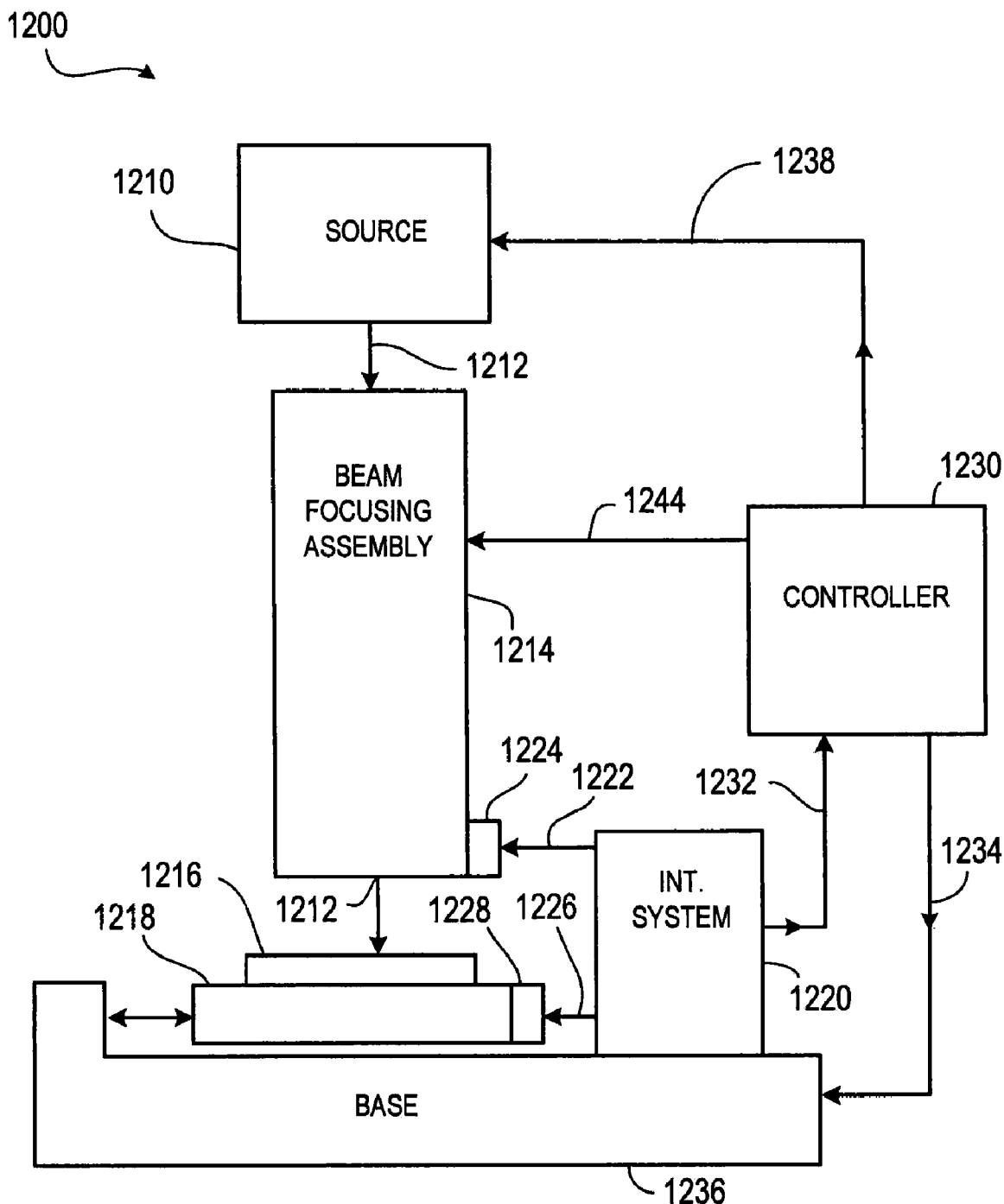
FIG. 9 is a schematic of a beam writing system that includes an interferometry system.

As an example, a schematic of a beam writing system 1200 is shown in FIG. 9. A source 1210 generates a write beam 1212, and a beam focusing assembly 1214 directs the radiation beam to a substrate 1216 supported by a movable stage 1218. To determine the relative position of the stage, an interferometry system 1220 directs a reference beam 1222 to a mirror 1224 mounted on beam focusing assembly 1214 and a measurement beam 1226 to a mirror 1228 mounted on stage 1218. Since the reference beam contacts a mirror mounted on the beam focusing assembly, the beam writing system is an example of a system that uses a column reference. Interferometry system 1220 can be any of the interferometry systems described previously. Changes in the position measured by the interferometry system correspond to changes in the relative position of write beam 1212 on substrate 1216. Interferometry system 1220 sends a measurement signal 1232 to controller 1230 that is indicative of the relative position of write beam 1212 on substrate 1216. Controller 1230 sends an output signal 1234 to a base 1236 that supports and positions stage 1218. In addition, controller 1230 sends a signal 1238 to source 1210 to vary the intensity of, or block, write beam 1212 so that the write beam contacts the substrate with an intensity sufficient to cause photophysical or photochemical change only at selected positions of the substrate.

Furthermore, in some embodiments, controller 1230 can cause beam focusing assembly 1214 to scan the write beam over a region of the substrate, e.g., using signal 1244. As a result, controller 1230 directs the other components of the system to pattern the substrate. The patterning is typically based on an electronic design pattern stored in the controller. In some applications the write beam patterns a resist coated on the substrate and in other applications the write beam directly patterns, e.g., etches, the substrate.

An important application of such a system is the fabrication of masks and reticles used in the lithography methods described previously. For example, to fabricate a lithography mask an electron beam can be used to pattern a chromium-coated glass substrate. In such cases where the write beam is an electron beam, the beam writing system encloses the electron beam path in a vacuum. Also, in cases where the write beam is, e.g., an electron or ion beam, the beam focusing assembly, e.g., includes electric field generators such as quadrapole lenses for focusing and directing the charged particles onto the substrate under vacuum. In other cases where the write beam is a radiation beam, e.g., x-ray, V, or visible radiation, the beam focusing assembly includes corresponding optics and for focusing and directing the radiation to the substrate.

Other embodiments are in the following claims.

What is claimed is:

1. A method, comprising:
    conditioning a first input beam and a second input beam, wherein conditioning the first and second input beams comprises directing the first and second input beams to reflect from a measurement object;
    forming a conditioned output beam from the conditioned first input beam and the conditioned second input beam, the conditioned output beam comprising a first interferometric phase comprising information about an optical path difference between the conditioned first input beam and the conditioned second input beam;
    deriving a first measurement beam and a first reference beam from the conditioned first input beam and conditioned second input beam, respectively, using an optical assembly and directing the first measurement beam to reflect from the measurement object remote from the optical assembly, wherein the conditioning causes the first measurement beam to be normally incident on the measurement object for a range of orientation angles of the measurement object with respect to the optical assembly, combining the first measurement beam and the first reference beam to form a first output beam comprising a second interferometric phase comprising information about an optical path difference between the first reference and measurement beams;
    detecting the conditioned output beam and the first output beam and monitoring the first and second interferometric phases based on the detected conditioned output beam and first output beam, respectively;
    monitoring a degree of freedom of the measurement object based the second interferometric phase; and
    reducing uncertainty in the monitored degree of freedom due to variations in the optical properties of a gas between the optical assembly and the measurement object based on the information from the first and second interferometric phases.

2. The method of claim 1, wherein the first input beam is directed to reflect from the measurement object twice.

3. The method of claim 2, wherein conditioning the first input beam causes the conditioned first input beam to be perpendicular to the measurement object for a range of orientation angles of the measurement object with respect to the optical assembly when it reflects from the measurement object the second time.

4. The method of claim 2, wherein conditioning the first input beam comprises directing the first input beam through an elliptical aperture.

5. The method of claim 1, wherein the first input beam and the second input beam are directed to reflect from the measurement object along parallel paths.

6. The method of claim 1, wherein the second input beam is directed to reflect from the measurement object twice.

7. The method of claim 6, wherein the first input beam path on its first pass to the measurement object is co-planar with the second input beam path on its second pass to the measurement object.

8. The method of claim 7, wherein the first input beam is directed to reflect from the measurement object twice and the first input beam path on its second pass to the measurement object is co-planar with the second input beam path on its first pass to the measurement object.

9. The method of claim 1, wherein the first and second interferometric phases comprise information about imperfections in a surface of the measurement object and reducing uncertainty comprises reducing uncertainty due to the imperfections based on the information from the first and second interferometric phases.

10. The method of claim 1, wherein the first input beam and the second input beam are derived from a common source.

11. The method of claim 1, further comprising flowing gas between the measurement object and the optical assembly.

12. The method of claim 8, wherein the gas is flowed in a direction substantially perpendicular to the measurement beam path.

13. The method of claim 11, wherein the first and second input beams are directed along corresponding paths to reflect a first time from the measurement object and the gas is flowed parallel to a plane defined the paths.

14. The method of claim 1, wherein the first interferometric phase comprises a term proportional to a spatial derivative of a term characterizing optical properties of the gas in the path of the first input beam between the optical assembly and the measurement object.

15. The method of claim 1, further comprising:
deriving a second measurement beam and a second reference beam from the conditioned second input beam and conditioned first input beam, respectively, using the optical assembly and directing the second measurement beam to reflect from the measurement object;
combining the second measurement beam and the second reference beam to form a second output beam comprising a third interferometric phase including information about an optical path difference between the second reference and second measurement beams;
detecting the second output beam and monitoring the third interferometric phase based on the detected second output beam,
wherein the first and second input beams are derived from a common source.

16. The method of claim 15, wherein reducing uncertainty in the monitored degree of freedom comprises determining values of a first difference parameter from the second and third interferometric phases.

17. The method of claim 16, further comprising determining information about a surface figure of the measurement object based on the values of the first difference parameter.

18. The method of claim 16, wherein reducing uncertainty in the monitored degree of freedom comprises inverting the values of the first difference parameter to obtain information about contributions of variations in the optical properties of the gas to the monitored interferometric phases of the first and second output beams.

19. The method of claim 18, wherein inverting the values comprises using a Fourier series or Fourier transform technique.

20. The method of claim 19, wherein a spacing between locations on the measurement object between the first and second measurement beams are selected so that a region of low sensitivity of the Fourier series or Fourier transform technique corresponds to a frequency region where contributions of acoustic perturbations and turbulence to the monitored second and third interferometric phases is minimal.

21. A lithography method for use in fabricating integrated circuits on a wafer, the method comprising:
supporting the wafer on a moveable stage;
imaging spatially patterned radiation onto the wafer;
adjusting the position of the stage; and
monitoring the position of the stage using the method of claim 1, wherein the measurement object is attached to the stage and the position of the stage is monitored from the monitored degree of freedom of the measurement object with reduced uncertainty.

22. A lithography method for fabricating integrated circuits on a wafer comprising:
positioning a first component of a lithography system relative to a second component of a lithography system to expose the wafer to spatially patterned radiation; and
monitoring the position of the first component relative to the second component using the method of claim 1, wherein the measurement object is attached to the first component and the position of the first component is monitored from the monitored degree of freedom of the measurement object with reduced uncertainty.

23. A method, comprising:
directing a first input beam and a second input beam to reflect from a measurement object;
forming a first output beam from the first input beam after it reflects from the measurement object by combining the first input beam with the second input beam, the first output beam comprising a first interferometric phase comprising information about an optical path difference between the first and second input beams;
deriving a first measurement beam from the first input beam and deriving a first reference beam from the second input beam using an optical assembly and directing the first measurement beam to reflect from the measurement object;
combining the first measurement beam and the first reference beam to form a second output beam comprising a second interferometric phase comprising information about an optical path difference between the first reference and measurement beams;
detecting the first and second output beams and monitoring the first and second interferometric phases based on the detected output beams;
monitoring a degree of freedom of the measurement object based the second interferometric phase; and
reducing uncertainty in the monitored degree of freedom due to variations in the optical properties of a gas between the optical assembly and the measurement object based on the information from the first and second interferometric phases.

24. A system, comprising:
a light source configured to produce a primary beam;
a beam conditioning assembly configured to receive the primary beam, to derive a first input beam and a second input beam from the primary beam, to direct the first and second input beams to reflect from a measurement object at least once, and to output a first conditioned input beam and a second conditioned input beam;
an interferometer assembly remote from the measurement object, the interferometer assembly being configured to receive the first and second conditioned input beams, to derive a first measurement beam from the first conditioned input beam and a first reference beam from the second conditioned input beam, to direct the first measurement and reference beams along different paths where the first measurement beam reflects from the measurement object, the interferometer assembly being further configured to combine the first measurement and reference beams to produce a first output beam comprising a first interferometric phase comprising information about a degree of freedom of the measurement object;

a first detector configured to detect the first output beam; and an electronic processor in communication with the first detector, the electronic processor being configured to determine information about the degree of freedom of the measurement object based on the interference phase of at least one of the output beams and to reduce uncertainty in the degree of freedom due to variations in the optical properties of a gas between the interferometer assembly and the measurement object based on the first interferometric phase.

25. The system of claim 24, wherein the beam conditioning assembly is configured to direct the first and second input beams to reflect from the measurement object twice.

26. The system of claim 25, wherein for a range of orientation angles of the measurement object with respect to the interferometry assembly, the first and second input beams are normally incident on the measurement object upon the second reflection from the measurement object.

27. The system of claim 24, wherein the interferometer assembly is configured to derive a second measurement beam from the second conditioned input beam and a second reference beam from the first conditioned input beam, to direct the second measurement and reference beams along different paths where the second measurement beam reflects from the measurement object, the interferometer assembly being further configured to combine the second measurement and reference beams to produce a second output beam comprising an interferometric phase comprising information about a second degree of freedom of the measurement object.

28. The system of claim 27, further comprising a second detector configured to detect the second output beam, the second detector being in communication with the electronic processor.

29. The system of claim 27, wherein the paths of the first and second measurement beams are parallel between the interferometer assembly and the measurement object.

30. The system of claim 24, wherein the beam conditioning assembly is further configured to derive a conditioned output beam from each of the first and second conditioned input beams and to combine the two conditioned output beams to provide a combined conditioned output beam, the combined conditioned output beam comprising an interferometric phase comprising information about an optical path difference between the first conditioned input beam and the second conditioned input beam.

31. The system of claim 30, wherein the conditioned output beam comprises a second interferometric phase comprising information about variations in the optical properties of a gas in the paths of the two conditioned input beams.

32. The system of claim 31, further comprising a detector configured to detect the conditioned output beam, the detector being in communication with the electronic processor, wherein the electronic processor is configured to reduce uncertainty in the degree of freedom due to variations in the optical properties of a gas between the interferometer assembly and the measurement object based on the second interferometric phase.

33. The system of claim 24, wherein the interferometry assembly directs the first measurement beam to reflect from the measurement object only once.

34. The system of claim 33, wherein the beam conditioning assembly is configured so that for a range of orientation angles of the measurement object with respect to the interferometry assembly, the first measurement beam is normally incident on the measurement object for the second reflection.

35. The system of claim 24, wherein the measurement object is a plane mirror measurement object.

36. The system of claim 24, wherein the measurement object is attached to a wafer stage of a lithography tool.

37. The system of claim 36, wherein the interferometry assembly and beam conditioning assembly are attached to frame of the lithography tool.

38. A lithography system for use in fabricating integrated circuits on a wafer, the system comprising:

an illumination system for imaging spatially patterned radiation onto the wafer;

the system of claim 24 configured to monitor a position of the wafer relative to the imaged radiation, wherein wafer is supported by a moveable stage and the measurement object is attached to the stage; and a positioning system for adjusting the position of the stage relative to the imaged radiation.

39. The lithography system of claim 38, wherein the lithography system is a dual stage lithography system.

40. A lithography system for use in fabricating integrated circuits on a wafer, the system comprising:

an illumination system including a radiation source, a mask, a positioning system, a lens assembly, and the system of claim 24, wherein during operation the source directs radiation through the mask to produce spatially patterned radiation, the positioning system adjusts the position of the mask relative to the radiation from the source, the lens assembly images the spatially patterned radiation onto the wafer supported by the stage, and the system monitors the position of the mask relative to the radiation from the source.

* * * * *